US011156686B2

(12) United States Patent
Mougenot

(10) Patent No.: US 11,156,686 B2
(45) Date of Patent: Oct. 26, 2021

(54) ACOUSTIC RADIATION FORCE IMAGING

(71) Applicant: KONINKLIJKE PHILIPS N.V., Eindhoven (NL)

(72) Inventor: Charles Mougenot, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 836 days.

(21) Appl. No.: 15/552,516

(22) PCT Filed: Feb. 25, 2016

(86) PCT No.: PCT/EP2016/053930
§ 371 (c)(1),
(2) Date: Aug. 22, 2017

(87) PCT Pub. No.: WO2016/139113
PCT Pub. Date: Sep. 9, 2016

(65) Prior Publication Data
US 2018/0024213 A1 Jan. 25, 2018

(30) Foreign Application Priority Data
Mar. 4, 2015 (EP) .................................... 15157560

(51) Int. Cl.
*G01R 33/48* (2006.01)
*G01R 33/563* (2006.01)
(Continued)

(52) U.S. Cl.
CPC .......... *G01R 33/4814* (2013.01); *A61N 7/02* (2013.01); *G01R 33/56308* (2013.01); *A61B 2090/374* (2016.02)

(58) Field of Classification Search
None
See application file for complete search history.

(56) References Cited

U.S. PATENT DOCUMENTS 8,155,725 B2  4/2012  Pernot et al.
8,427,154 B2  4/2013  Salomir et al.
(Continued)

OTHER PUBLICATIONS

Herzberg et al. (2010). Ultrasound focusing using magnetic resonance acoustic radiation force imaging: Application to ultrasound transcranial therapy. Med. Phys. 37(6): 2934-2942 (Year: 2010).*
(Continued)

*Primary Examiner* — Bill Thomson
*Assistant Examiner* — Younhee Choi
(74) *Attorney, Agent, or Firm* — Sherry Austin

(57) ABSTRACT

An apparatus includes a high intensity focused ultrasound (HIFU) system and a magnetic resonance (MR) imaging system. A memory stores: instructions, pulse sequence commands for an acoustic radiation force imaging protocol, and first and second sonication commands. The pulse sequence commands specify acquisition of the MR data for first and second pulse sequence repetitions. The pulse sequence commands specify for each of the sequence repetitions a first and a second group of motion encoding gradients. Execution of the instructions causes a processor to: acquire first and second MR data by controlling the MR imaging system with the pulse sequence commands and by controlling the HIFU system with the first and second sonication commands, respectively; reconstruct first and second motion encoded images from the first and second MR data, respectively; and construct a displacement map from the difference of the first and second motion encoded images.

20 Claims, 16 Drawing Sheets

(51) Int. Cl.
*A61N 7/02* (2006.01)
*A61B 90/00* (2016.01)

(56) References Cited

U.S. PATENT DOCUMENTS

| | | | |
|---|---|---|---|
| 9,146,290 B2 | 9/2015 | Ylihautala | |
| 9,226,683 B2* | 1/2016 | Gross | G01R 33/5673 |
| 9,579,042 B2 | 2/2017 | Zur | |
| 10,459,043 B2 | 10/2019 | Vahala | |
| 2007/0167705 A1* | 7/2007 | Chiang | G01R 33/28 |
| | | | 600/407 |
| 2011/0094288 A1* | 4/2011 | Medan | G10K 11/346 |
| | | | 73/1.82 |
| 2013/0023862 A1* | 1/2013 | Marrouche | A61N 7/02 |
| | | | 606/3 |
| 2013/0345547 A1* | 12/2013 | Vahala | G01R 33/56358 |
| | | | 600/411 |
| 2014/0112095 A1 | 4/2014 | Medan et al. | |
| 2015/0080705 A1 | 3/2015 | Partanen | |
| 2015/0190659 A1 | 7/2015 | Kohler | |
| 2016/0045771 A1 | 2/2016 | Kohler | |

OTHER PUBLICATIONS

McDannold et al "Magnetic Resonance Acoustic Radiation Force Imaging" Medical Physics vol. 35, Aug. 2008 p. 3748-3758.

Auboiroux et al "ARFI-Prepared MRgHIFU in Liver: Simultaneous Mapping of ARFI-Displacement and Temperature Evevation . . . " Magnetic Resonance in Med. 89: p. 932-046 (2012).

Hertzberg et al "Ultrasound Focusing Magnetic Resonance Acoustic Radiation Force Imaging." Med.Phys. 37 (2010).

Kaye, E. A. and Pauly, K. B. (2013), Adapting MRI acoustic radiation force imaging for in vivo human brain focused ultrasound applications. Magn Reson Med, 69: 724-733. doi: 10.1002/mrm.24308.

Holbrook et al "In Vivo MR Acoustic Radiation Force Imaging in the Procine Liver" Med Phys. 38(9) Sep. 2011, p. 5081-5089.

Chen et al "Optimization of encoding gradients for MR-ARFI" Magn Reson Med. Apr. 2010;63(4):1050-8.

Kaye "Rapid MR-ARFI Method for Focal Spot Localization During Focused Ultrasound Therapy" Magnetic Resonance in Medicine 65:738-743 (2011).

Marsac et al "MR-guided adaptive focusing of therapeutic ultrasound beams in the human head" Med Phys. Feb. 2012; 39(2):1141-9.

Chen J. et al., "MR Acoustic Radiation Force Imaging: Comparision of Encoding Gradients", Proceedings of the 16th Scientific Meting, International Society for magnetic Resonance in Medicine, Toronto, ON, 2208, p. 1240.

* cited by examiner

ACOUSTIC RADIATION FORCE IMAGING

CROSS REFERENCE TO RELATED APPLICATIONS

This application is a U.S. national phase application of International Application No. PCT/EP2016/053930, filed on Feb. 25, 2016, which claims the benefit of EP Application Serial No. 15157560.2 filed on Mar. 4, 2015 and is incorporated herein by reference.

TECHNICAL FIELD OF THE INVENTION

The invention relates to magnetic resonance guided high intensity focused ultrasound, in particular it relates to the determination of tissue displacement by high intensity focused ultrasound using magnetic resonance imaging.

BACKGROUND OF THE INVENTION

In high intensity focused ultrasound (HIFU) an array of ultrasonic transducer elements are used to form an ultrasonic transducer. Supplying alternating current electrical power to the transducer elements causes them to generate ultrasonic waves. The ultrasonic waves from each of the transducer elements either add constructively or destructively at different locations in the beam path. By controlling the phase of alternating current electrical power supplied to each of the transducer elements the focal point or volume into which the ultrasound power is focused may be controlled.

High-intensity focused ultrasound (HIFU) therapy of tumors requires a high degree of spatial accuracy in order to avoid damaging healthy tissue as well as to obtain optimal usage of the system. Although avoiding damaging healthy tissue due to poor targeting is typically not a problem for large stationary tumors if utilizing low-power test sonications as is current practice, the technical performance and/or clinical performance of the system may suffer if incorrect positional knowledge is used for a feedback algorithm for example. This translates into reduced treatment efficiency.

Magnetic resonance (MR) acoustic radiation force imaging (MR-ARFI) may be used to observe the radiation force that mechanical pressure waves exert on in vivo tissue. This for example includes the estimation of the radiation force exerted by absorbed high-intensity focused ultrasound.

The journal article *"Magnetic resonance acoustic radiation force imaging"* by McDannold and Maier published in Medical Physics volume 35, August 2008, pages 3748 to 3758 discloses an elastographic method of determining the displacement cause by focused ultrasound using magnetic resonance imaging.

The journal article *"ARFI-Prepared MRgHIFU in Liver: Simultaneous Mapping of ARFI-Displacement and Temperature elevation, Using a Fast GRE-EPI Sequence,"* by Auboiroux et. al. published in Magnetic Resonance in Medicine 68:932-946 (2012), pages 932 through 946 discloses a combination of MR-ARFI with proton resonance frequency shift MR thermometry.

The paper *'Ultrasound focusing magnetic resonance acoustic radiation force imaging: Application to ultrasound transcranial therapy'* by Y. Hertzberg et al. in Med.Phys.37 (2010)2934 concerns a gradient echo MR-ARFI sequence. This sequence has motion encoding gradients in which the polarities of the gradient (waveforms) is inverted.

SUMMARY OF THE INVENTION

The invention provides for a medical apparatus, a method of operating the medical apparatus and a computer program product in the independent claims. Embodiments are given in the dependent claims. As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD), Digital Versatile Disks (DVD), and Blu-Ray Disc (BD), for example CD-ROM, CD-RW, CD-R, DVD-ROM, DVD-RW, DVD-R, BD-R, or BD-RE disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Medical image data is defined herein as two or three dimensional data that has been acquired using a medical imaging scanner. A medical imaging scanner is defined herein as an apparatus adapted for acquiring information about the physical structure of a patient and construct sets of two dimensional or three dimensional medical image data. Medical image data can be used to construct visualizations which are useful for diagnosis by a physician. This visualization can be performed using a computer.

Magnetic Resonance (MR) data is defined herein as being the recorded measurements of radio frequency signals emitted by atomic spins by the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer.

Magnetic resonance data may comprise the measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonance frequency.

The proton density depends linearly on the equilibrium magnetization. It is therefore possible to determine temperature changes using proton density weighted images.

The relaxation times T1, T2, and T2-star (sometimes written as T2*) are also temperature dependent. The reconstruction of T1, T2, and T2-star weighted images can therefore be used to construct thermal or temperature maps.

The temperature also affects the Brownian motion of molecules in an aqueous solution. Therefore pulse sequences which are able to measure diffusion coefficients such as a pulsed diffusion gradient spin echo may be used to measure temperature.

One of the most useful methods of measuring temperature using magnetic resonance is by measuring the proton resonance frequency (PRF) shift of water protons. The resonance frequency of the protons is temperature dependent. As the temperature changes in a voxel the frequency shift will cause the measured phase of the water protons to change. The temperature change between two phase images can therefore be determined. This method of determining temperature has the advantage that it is relatively fast in comparison to the other methods.

An 'ultrasound window' as used herein encompasses a window which is effectively transparent to ultrasonic waves or energy. Typically a thin film or membrane is used as an ultrasound window. The ultrasound window may for example be made of a thin membrane of BoPET (Biaxially-oriented polyethylene terephthalate).

In one aspect the invention provides for a medical apparatus comprising a high-intensity focused ultrasound system for sonicating a sonication region. The medical apparatus further comprises a magnetic resonance imaging system for acquiring magnetic resonance data from an imaging zone. The magnetic resonace data could be considered to be acquired as divided into first magnetic resonance data and second magnetic resonance data. The sonication region and the imaging zone at least partially overlap. In some examples the sonication region could be completely within the imaging zone. In other examples the sonication region has at least a part of it outside of the imaging zone. Depending upon the application the sonication region may have a different size or dimension. In some examples the sonication region would just include the point where the high-intensity focused ultrasound is focused. In other examples the sonication region may include the near field or even the far field of the ultrasound. The medical apparatus further comprises a processor for controlling the medical apparatus.

The medical apparatus further comprises a memory for storing machine-executable instructions. The memory further stores pulse sequence commands for controlling the magnetic resonance imaging system to acquire magnetic resonance data according to an acoustic radiation force imaging protocol. The pulse sequence commands as used herein comprise commands which are descriptive of or may be used for directly controlling the magnetic resonance imaging system to acquire the magnetic resonance data. Typically the protocols for magnetic resonance imaging are defined in terms of a so called pulse sequence. The pulse sequence is a timing diagram which shows the actions that various components of the magnetic resonance imaging system take at various times. The pulse sequence commands may also encompass the idea of a timing diagram such as a pulse sequence that may be readily converted into commands for controlling the magnetic resonance imaging system.

The memory further stores first sonication commands and second sonication commands. Both the first sonication commands and the second sonication commands are commands which are used to control the high-intensity focused ultrasound system to sonicate the sonication region according to the acoustic radiation force imaging protocol. That is to say the sonication commands cause the high-intensity focused ultrasound system to sonicate the sonication region during motion encoding gradients such that the acoustic radiation force imaging protocol can be applied. The pulse sequence commands specify the acquisition of the magnetic resonance data for multiple pulse sequence repetitions. The pulse sequence commands specifies for each of the multiple sequence repetitions a first group of motion encoding gradients and a second group of motion encoding gradients. During an acoustic radiation force imaging protocol motion encoding gradients are applied when there is a sonication of the sonication region and when there is no sonication. The data from these two sets is compared and this is used to determine the motion due to the applied ultrasound.

Execution of the machine-executable instructions cause the processor to acquire first magnetic resonance data by controlling the magnetic resonance imaging system with the pulse sequence commands and by controlling the high-intensity focused ultrasound system with the first sonication commands. The first sonication commands cause the high-intensity focused ultrasound system to sonicate the sonication region during the first group of motion encoding gradients. Execution of the machine-executable instructions further cause the processor to acquire second magnetic resonance data by controlling the magnetic resonance imaging system with the pulse sequence commands and by controlling the high-intensity focused ultrasound system with the second sonication commands.

The second sonication commands cause the high-intensity focused ultrasound system to sonicate the sonication region during the second group of motion encoding gradients. When applying conventional acoustic radiation force imaging protocols the state of the art protocols use sonication pulses at the same point within the protocol and the motion encoding gradients are changed. In this example the pulse sequence used to acquire both the first magnetic resonance data and the second magnetic resonance data are identical. Instead of changing the pulse sequence for controlling the magnetic resonance imaging system the sonication occurs at different points within the identical pulse sequences.

Execution of the machine-executable instructions further cause the processor to reconstruct a first motion encoded image from the first magnetic resonance data. Execution of the machine-executable instructions further cause the processor to reconstruct a second motion encoded image from the second magnetic resonance data. Execution of the machine-executable instructions further cause the processor to construct a displacement map from the difference of the first motion encoded image and the second motion encoded image.

This example may have the benefit that the pulse sequence executed by the magnetic resonance imaging system is identical every time. Changing the pulse sequence can lead to a variety of problems. For example the switching of motion encoding gradients polarity during every dynamic may be a source of multiple image artifacts such as from eddy currents and the rupture of the magnetic resonance image steady state. As a result application of this example may result in higher quality acoustic radiation force images. The displacement map that is produced may have fewer artifacts. As used herein, a dynamic refers to a portion of a pulse sequence repetition.

In another embodiment execution of the machine executable instructions cause the processor to construct a magnetic resonance image from the first and or second magnetic resonance data. In some examples the displacement map or even a thermal map may be superimposed on the magnetic resonance image.

In another embodiment the pulse sequence commands encode for displacement in a first direction during the first group of motion encoding gradients. The pulse sequence commands encode for displacement in a second direction during the second group of motion encoding gradients. The first direction is opposite to the second direction.

In another embodiment the acoustic radiation force imaging protocol is a gradient echo acoustic radiation force imaging protocol.

In another embodiment the pulse sequence commands specify that the first group of motion encoding gradients has a first polarity and that the second group of motion encoding gradients has a second polarity. The first polarity and the second polarity are opposite.

In another embodiment execution of the machine-executable instructions further causes the processor to calculate a thermal map using the first magnetic resonance data and the second magnetic resonance data according to a proton resonance frequency shift method. Performing this may be advantageous because an accurate thermal map may be compared to the improved displacement map.

In another embodiment the acoustic radiation force imaging protocol is a spin echo acoustic radiation force imaging protocol.

In another embodiment the pulse sequence commands specify that the first group of motion encoding gradients has a first polarity and the second group of motion encoding gradients has the first polarity. The polarity refers to the direction of the magnetic field produced by the gradients or it may also refer to the current that is applied to the motion encoding gradients. In other words this states that the first group of motion encoding gradients and the second group of motion encoding gradients have magnetic fields or current that is applied with the same polarity. For each individual group of motion encoding gradients, the wavefrom of the motion encoding gradients may be a multi-polar group of gradient lobes, each gradient lobe having a gradient orientation and the waveform of eh motion encoding gradient pulse having a polarity pattern made up by the several gradient lobes. A particular example is a bipolar waveform of two gradient lobes of opposite (individual) gradient orientations. These gradient orientations of the multi-polar motion encoding gradients make up the polarity of the motion encoding gradients' waveform formed by its gradient lobes as a whole.

In another embodiment the acoustic radiation force imaging protocol is a spin echo acoustic radiation force imaging protocol with static unipolar gradients.

In another embodiment the pulse sequence commands specify that the first group of motion encoding gradients is divided into a first part and a second part. The pulse sequence commands specify that the second group of motion encoding gradients is divided into a third part and a fourth part. The pulse sequence commands specify that the first part and the second part have opposite polarities. The pulse sequence commands specify that the third part and the fourth part have opposite polarities. The pulse sequence commands specify that the first part and the fourth part have identical polarities. Again, the polarity of the motion encoding gradients may be defined in terms of the direction of the field produced or in terms of the current supplied to the coils. It may be possible that the first part occurs before the second part. Likewise, it is also possible that the fourth part occurs before the third part.

When referring to the first group of motion encoding gradients and the second group of motion encoding gradients, it is also possible that the second group of motion encoding gradients occurs temporally before the first group of motion encoding gradients. Specifying the gradients as groups or parts does not imply a particular order.

In another embodiment the acoustic radiation force imaging protocol is a spin echo acoustic radiation force imaging protocol with static bipolar gradients.

In another embodiment the pulse sequence commands specify a predetermined pause of the motion encoding gradients between the first part and the third part. The pulse sequence commands specify a predetermined pause of the motion encoding gradients between the second part and the fourth part. This predetermined pause may be beneficial because the displacement of the ultrasound induced in the subject does not instantaneously go up and go down again. There is a build up time and a time which it takes for the ultrasound displacement to decay. By having a predetermined pause between the first part and the third part and also between the second part and the fourth part enables for the decay of the ultrasound to occur so that sonication does not occur during the wrong motion encoding gradient.

In another embodiment the predetermined pause is between 1 ms and 20 ms.

In another embodiment the predetermined pause is between 2 ms and 4 ms.

In another embodiment the predetermined pause is between 3 ms and 5 ms.

In another embodiment the predetermined pause is between 4 ms and 6 ms.

A predetermined pause of approximately 4 ms may useful because the exponential decay rate of the ultrasound is typically in the neighborhood of 5 ms. A pause of at least 1 ms may be beneficial in some cases and this may also be increased up to the point where the motion encoding gradients reach the imaging readout gradient. In general practice a predetermined pause of about 1 ms to 20 ms may be particularly useful.

In another embodiment the pulse sequence commands specify a predetermined delay of the motion encoding gradients between the first group of motion encoding gradients and the second group of motion encoding gradients. The predetermined delay may be useful due to the previously mentioned build up time and exponential decay rate of the ultrasound within the subject. Having a predetermined delay may reduce the effects of the sonication energy being falsely encoded into the wrong group of motion encoding gradients.

As with the above discussion the predetermined delay between 1 ms and 20 ms may also be useful for the predetermined delay.

In another embodiment the predetermined delay is between 1 ms and 20 ms.

In another embodiment the predetermined delay is between 2 ms and 4 ms.

In another embodiment the predetermined delay is between 3 ms and 5 ms.

In another embodiment the predetermined delay is between 4 ms and 6 ms.

In another embodiment any one of the following: the first part occurs before the second part, and the second part occurs before the first part.

In another embodiment execution of a machine-executable instructions cause the processor to perform any one of the following: acquire the first magnetic resonance data and the second magnetic resonance data sequentially, and acquire the first magnetic resonance data and the second magnetic resonance data by interleaving the acquisition of lines of k-space.

In another embodiment execution of the machine-executable instructions further cause the processor to receive a sonication pattern. Execution of the machine-executable instructions further cause the processor to modify the sonication pattern using the displacement map. This may be beneficial because the improved displacement map may be used to modify the sonication pattern to more accurately sonicate the subject. In some examples execution of the machine-executable instructions may also control the high-intensity focused ultrasound system to perform sonication after modifying the sonication plan. During the execution of the sonication of a subject various steps of the processors or methods discussed herein may be used repeatedly. For example during sonication the properties or elastic properties of the tissue of the subject may change. It may therefore be necessary to repeatedly go through the process of constructing the displacement map to accurately adjust the sonication pattern as a sonication is performed.

In another aspect the invention provides for a method of operating the medical apparatus. The medical apparatus comprises a high-intensity focused ultrasound system for sonicating a sonication region. The medical apparatus further comprises a magnetic resonance imaging system for acquiring magnetic resonance data from an imaging zone. The sonication region and the imaging zone at least partially overlap. The method comprises the step of acquiring first magnetic resonance data by controlling the magnetic resonance imaging system with pulse sequence commands and by controlling the high-intensity focused ultrasound system with the first sonication commands.

The pulse sequence commands control the magnetic resonance imaging system to acquire magnetic resonance data according to an acoustic radiation force imaging protocol. The pulse sequence specifies the acquisition of magnetic resonance data from multiple pulse sequence repetitions. The pulse sequence commands specifies for each of the multiple sequence repetitions a first group of motion encoding gradients and a second group of motion encoding gradients. The first sonication commands cause the high-intensity focused ultrasound system to sonicate the sonication region during the first group of motion encoding gradients according to the acoustic radiation force imaging protocol.

The method further comprises acquiring magnetic resonance data by controlling the magnetic resonance imaging system with the pulse sequence commands and by controlling the high-intensity focused ultrasound system with the second sonication commands. The second sonication commands cause the high-intensity focused ultrasound system to sonicate the sonication region during the second group of motion encoding gradients according to the acoustic radiation force imaging protocol. The method further comprises the step of reconstructing a first motion encoded image from the first magnetic resonance data. The method further comprises the step of reconstructing a second motion encoded image from the second magnetic resonance data. The method further comprises constructing a displacement map from the difference of the first motion encoded image and the second motion encoded image.

In another aspect the invention provides for a computer program product for execution by a processor controlling the medical apparatus. The medical apparatus comprises a high-intensity focused ultrasound system for sonicating a sonication region. The medical apparatus further comprises a magnetic resonance imaging system for acquiring magnetic resonance data from an imaging zone. The sonication region and the imaging zone at least partially overlap. Execution of the machine-executable instructions cause the processor to acquire first magnetic resonance data by controlling the magnetic resonance imaging system with the pulse sequence commands and by controlling the high-intensity focused ultrasound system with first sonication commands. The pulse sequence commands cause the magnetic resonance imaging system to acquire magnetic resonance data according to an acoustic radiation force imaging protocol. The pulse sequence specifies the acquisition of the magnetic resonance data for multiple pulse sequence repetitions. The pulse sequence commands specify for each of the multiple pulse sequence repetitions a first group of motion encoding gradients and a second group of motion encoding gradients.

The first sonication commands cause the high-intensity focused ultrasound system to sonicate the sonication region during the first group of motion encoding gradients according to the acoustic radiation force imaging protocol. Execution of the machine-executable instructions further cause the processor to acquire the second magnetic resonance data by controlling the magnetic resonance imaging system with the pulse sequence commands and by controlling the high-intensity focused ultrasound system with the second sonication commands. The second sonication commands cause the high-intensity focused ultrasound system to sonicate the sonication region during the second group of motion encoding gradients according to the acoustic radiation force imaging protocol. Execution of the machine-executable instructions further cause the processor to reconstruct a first motion encoded image from the first magnetic resonance data. Execution of the machine-executable instructions further cause the processor to reconstruct a second motion encoded image from the second magnetic resonance data. Execution of the machine-executable instructions further cause the processor to construct a displacement map for the difference of the first motion encoded image and the second motion encoded image.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
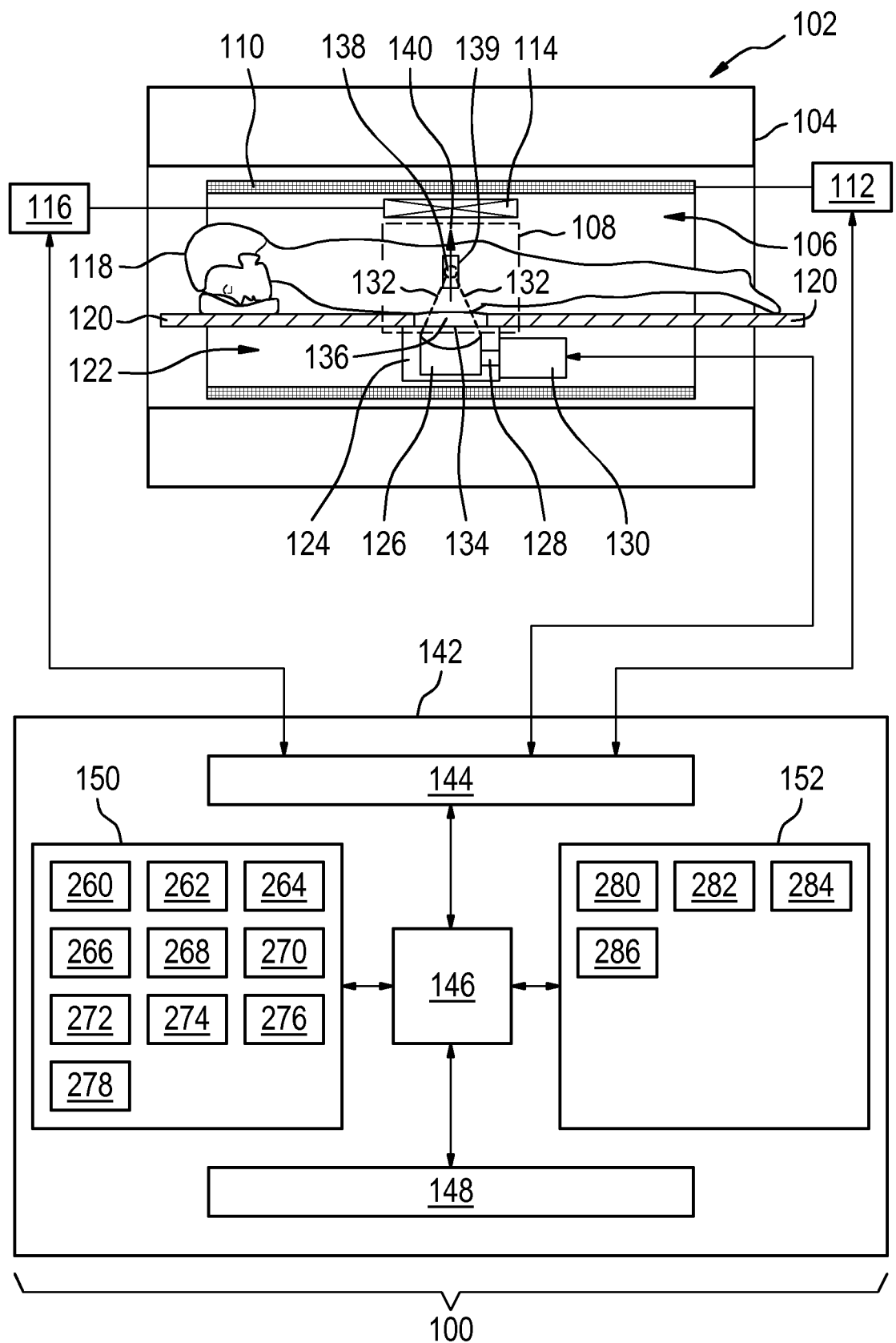
FIG. 1 illustrates an example of a medical apparatus.
Figure 2:
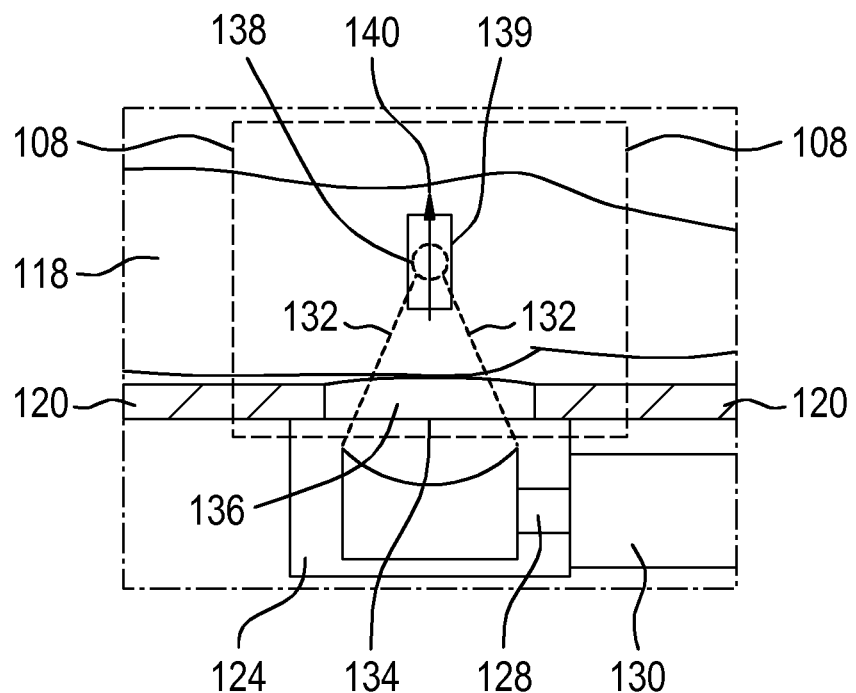
FIG. 2 shows an enlarged view of a portion of FIG. 1.

FIGS. 1 and 2 show a medical apparatus 100 according to an embodiment of the invention. FIG. 2 shows an enlarged view of a portion of FIG. 1. The medical apparatus 100 comprises a magnetic resonance imaging system 102. The magnetic resonance imaging system comprises a magnet 104. The magnet 104 is a cylindrical type superconducting magnet with a bore 106 through the center of it. The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet there is an imaging zone 108 where the magnetic field is strong and uniform enough to perform magnetic resonance imaging.

Within the bore 106 of the magnet there is also a set of magnetic field gradient coils 110 which are used for acquisition of magnetic resonance data to spatially encode magnetic spins within the imaging zone 108 of the magnet 104. The magnetic field gradient coils are connected to a magnetic field gradient coil power supply 112. The magnetic field gradient coils 110 are intended to be representative. Typically magnetic field gradient coils contain three separate sets of coils for spatially encoding in three orthogonal spatial directions. A magnetic field gradient power supply 112 supplies current to the magnetic field gradient coils 110. The current supplied to the magnetic field coils is controlled as a function of time and may be ramped or pulsed.

Adjacent to the imaging zone 108 is a radio-frequency coil 114 for manipulating the orientations of magnetic spins within the imaging zone 108 and for receiving radio transmissions from spins also within the imaging zone. The radio-frequency coil may contain multiple coil elements. The radio-frequency coil may also be referred to as a channel or an antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio-frequency transceiver 116 are representative. The radio-frequency coil 114 is intended to also represent a dedicated transmit antenna and a dedicated receive antenna. Likewise the transceiver 116 may also represent a separate transmitter and receivers.

A subject 118 is shown as reposing on a subject support 120 and is located partially within the imaging zone 108. The medical apparatus 100 also comprises a high-intensity focused ultrasound system 122. The high-intensity focused ultrasound system comprises a fluid-filled chamber 124. Within the fluid-filled chamber 124 is an ultrasound transducer 126. Although it is not shown in this figure the ultrasound transducer 126 may comprise multiple ultrasound transducer elements each capable of generating an individual beam of ultrasound. This may be used to steer the location of a sonication point 138 electronically by controlling the phase and/or amplitude of alternating electrical current supplied to each of the ultrasound transducer elements. Point 138 represents the adjustable focus of the medical apparatus 100.

The ultrasound transducer 126 is connected to a mechanism 128 which allows the ultrasound transducer 126 to be repositioned mechanically. The mechanism 128 is connected to a mechanical actuator 130 which is adapted for actuating the mechanism 128. The mechanical actuator 130 also represents a power supply for supplying electrical power to the ultrasound transducer 126. In some embodiments the power supply may control the phase and/or amplitude of electrical power to individual ultrasound transducer elements. In some embodiments the mechanical actuator/power supply 130 is located outside of the bore 106 of the magnet 104.

The ultrasound transducer 126 generates ultrasound which is shown as following the path 132. The ultrasound 132 goes through the fluid-filled chamber 128 and through an ultrasound window 134. In this embodiment the ultrasound then passes through a gel pad 136. The gel pad 136 is not necessarily present in all embodiments but in this embodiment there is a recess in the subject support 120 for receiving a gel pad 136. The gel pad 136 helps couple ultrasonic power between the transducer 126 and the subject 118. After passing through the gel pad 136 the ultrasound 132 passes through the subject 118 and is focused to a sonication point 138 or target zone. The arrow 140 indicates the beam axis. When ultrasound is applied to the target zone the subject will experience a force in the direction of the arrow 140. The sonication region 139 is indicated by the box 139. It is shown as encompassing the target zone 138 and a portion of the beam axis 140.

The sonication point 138 may be moved through a combination of mechanically positioning the ultrasonic transducer 126 and electronically steering the position of the sonication point 138 to treat the entire target volume 140.

The magnetic field gradient coil power supply 112, the transceiver 116, and the mechanical actuator/power supply 130 of the high-intensity focused ultrasound system 122 are shown as being connected to a hardware interface 144 of computer 142. The computer 142 further comprises a processor 146, a user interface 148, computer storage 150, and computer memory 152. The hardware interface 144 enables the processor 146 to send and receive commands and data in order to control the functioning of the medical apparatus 100. The processor 146 is further connected to the user interface 148, the computer storage 150, and the computer memory 152.

The computer storage 150 is shown as containing pulse sequence commands 260. The computer storage 150 is also shown as containing first sonication commands 262. The pulse sequence commands 260 can be used by the medical apparatus 100 to control the magnetic resonance imaging system 102 to acquire magnetic resonance data. The computer storage 150 is further shown as containing second sonication commands 264. The computer storage 150 is further shown as containing first magnetic resonance data 266 and second magnetic resonance data 268 that were both acquired using the magnetic resonance imaging system 102 controlled by the pulse sequence commands 260. The first sonication commands 262 were used with the pulse sequence command 260 during acquisition of the first magnetic resonance data 266. The second sonication commands 264 were used with the pulse sequence commands 260 to acquire the second magnetic resonance data 268.

The computer storage 150 is further shown as containing a first motion encoded image 270 that was reconstructed from the first magnetic resonance data 266. The computer storage 150 is further shown as containing a second motion encoded image 272 that was reconstructed from the second magnetic resonance data 268. The computer storage 150 is further shown as containing a displacement map 274 that was constructed by subtracting the first motion encoded image 270 from the second motion encoded image 272. The computer storage is further shown as containing an optional temperature map 276 that was reconstructed from the first magnetic resonance data 266 and/or the second magnetic resonance data 268. The computer storage is further shown as containing a sonication pattern 278. The sonication point 138 may be moved either mechanically or electronically to a variety of different sonication locations to form a sonication pattern 278.

The computer memory 152 is shown as containing a control module 280. The control module 280 contains code which enables the processor 146 to control the operation and function of the medical apparatus 100. For example the control module 280 may contain code which enables the processor 146 to use the pulse sequence commands 260 and/or the first sonication commands 262 or the second sonication commands 264. The computer memory 152 is further shown as containing a radiation force image reconstruction module 282 which may be used for constructing the first motion encoded image 270, the second motion encoded image 272 and the displacement map 274. The computer memory 152 may further contain optionally a magnetic resonance thermometry reconstruction module 284 which enables the construction of the temperature map 276 from the first magnetic resonance data and/or the second magnetic resonance data 268. The computer memory 152 is further shown as containing an optional sonication pattern modification module 286. The sonication pattern modification module 286 may modify the sonication pattern 278 to take into account the displacement map 274 and/or optionally the temperature map 276.

Figure 3:
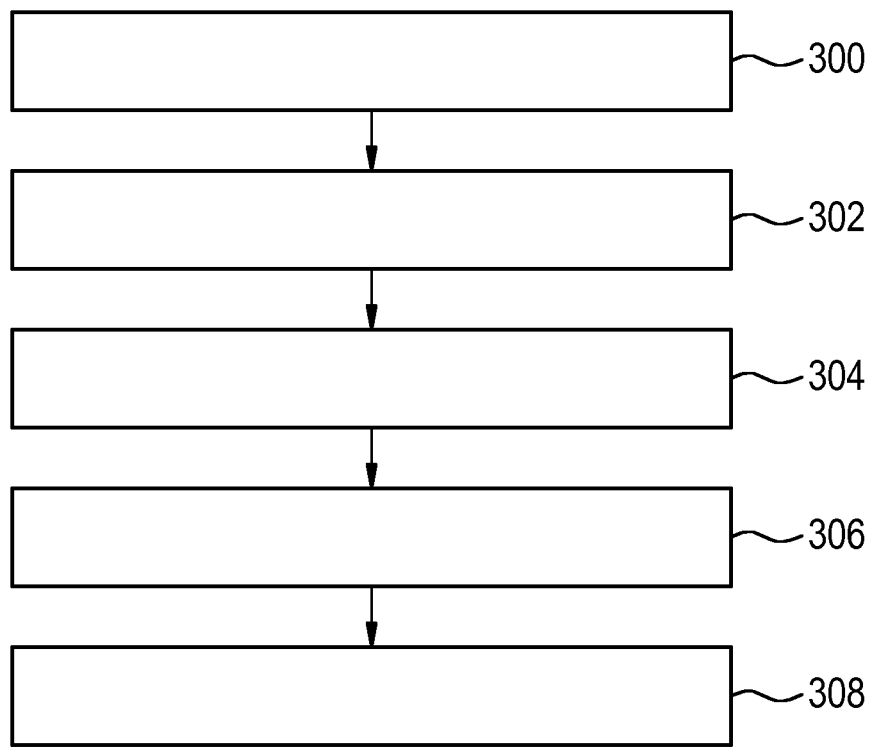
FIG. 3 shows a flow chart which illustrates a method of operating the medical apparatus of FIG. 1.

FIG. 3 shows a flowchart which illustrates an example of a method of controlling the medical apparatus 100 of FIGS. 1 and 2. First in step 300 the magnetic resonance imaging system 102 is controlled with the pulse sequence commands 260 to acquire the first magnetic resonance data 266. At the same time the processor 146 controls the high-intensity focused ultrasound system 122 with the first sonication commands 262. The first sonication commands cause the high-intensity focused ultrasound system to sonicate the sonication region during a first group of motion encoding gradients. Next in step 302 the pulse sequence commands 260 are used to control the magnetic resonance imaging system 102 to acquire the second magnetic resonance data 268. At the same time the high-intensity focused ultrasound system 122 is controlled with the second sonication commands 264. The second sonication commands 264 cause the high-intensity focused ultrasound system 122 to sonicate the sonication region 139 in the second group of motion encoding gradients. In step 304 a first motion encoded image 270 is reconstructed from the first magnetic resonance data 266. In step 306 a second motion encoded image 272 is reconstructed from the second magnetic resonance data 268. Finally in step 308 a displacement map 274 is constructed from the difference of the first motion encoded image 270 and the second motion encoded image 272.

Figure 4:
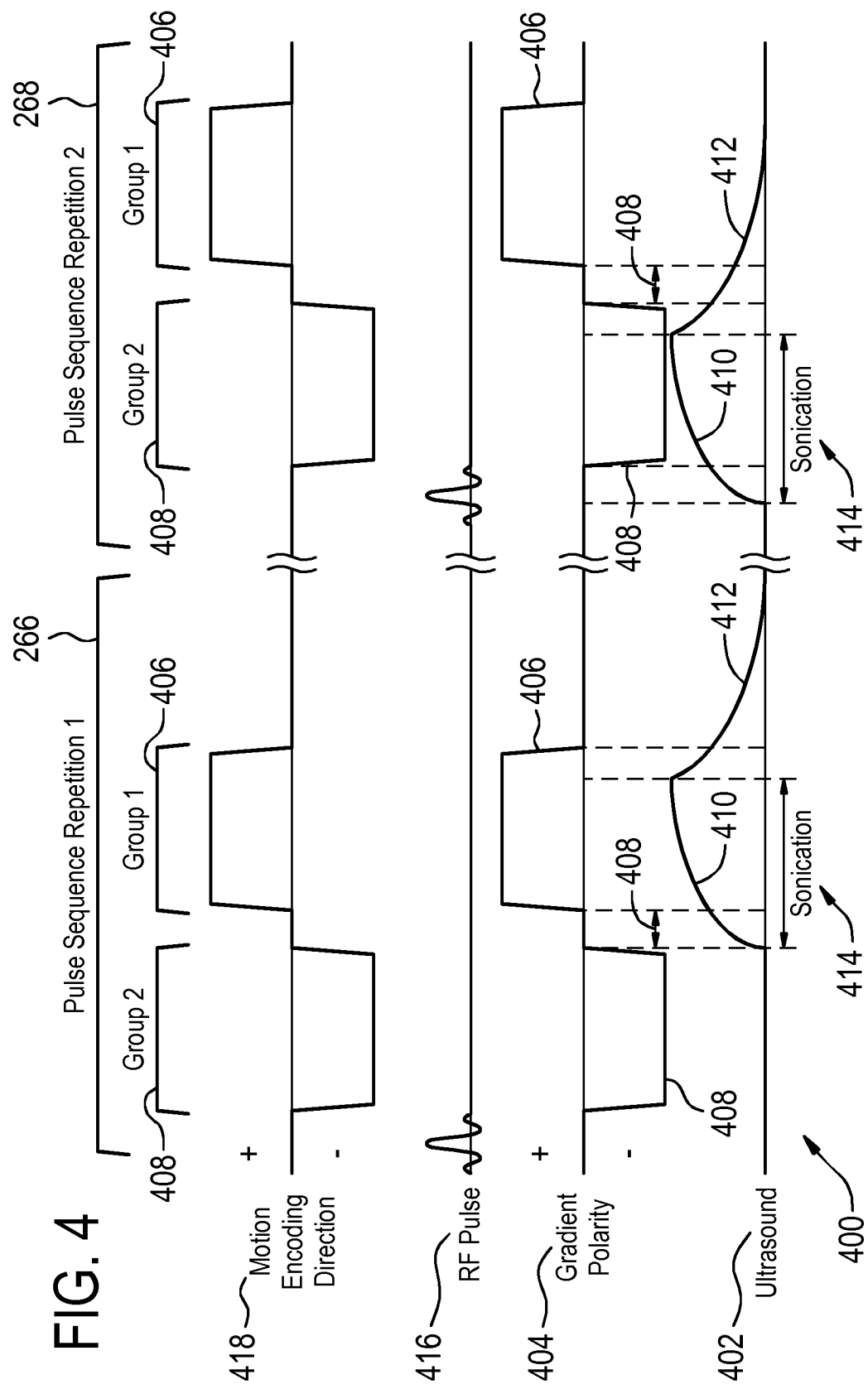
FIG. 4 shows a timing diagram which illustrates a gradient echo magnetic resonance ARFI sequence.

FIG. 4 shows a timing diagram 400 which illustrates a gradient echo magnetic resonance ARFI sequence. The line 402 shows when ultrasound is applied. Line 404 shows the gradient polarity which may be the direction of the current or the magnetic field generated. Line 416 shows when RF pulses are generated for the gradient echo. Line 418 shows the motion encoding direction of the particular gradient. The motion encoding gradients 404 are divided into a first group 406 and a second group 408. The ultrasound displacement has a rise 410 and a fall 412. There is a predetermined delay 408 between the first group 406 and the second group 408 in order for the ultrasound displacement to have time to build up or decay sufficiently to enable the method to be performed. It can be seen that there is a first pulse sequence repetition which acquires the first magnetic resonance data 266 and a second pulse sequence repetition which acquires the second magnetic resonance data 268. In this example it can be seen that between the two different pulse sequence repetitions the sonication is performed at a different temporal time relative to the rest of the pulse sequence.

Figure 5:
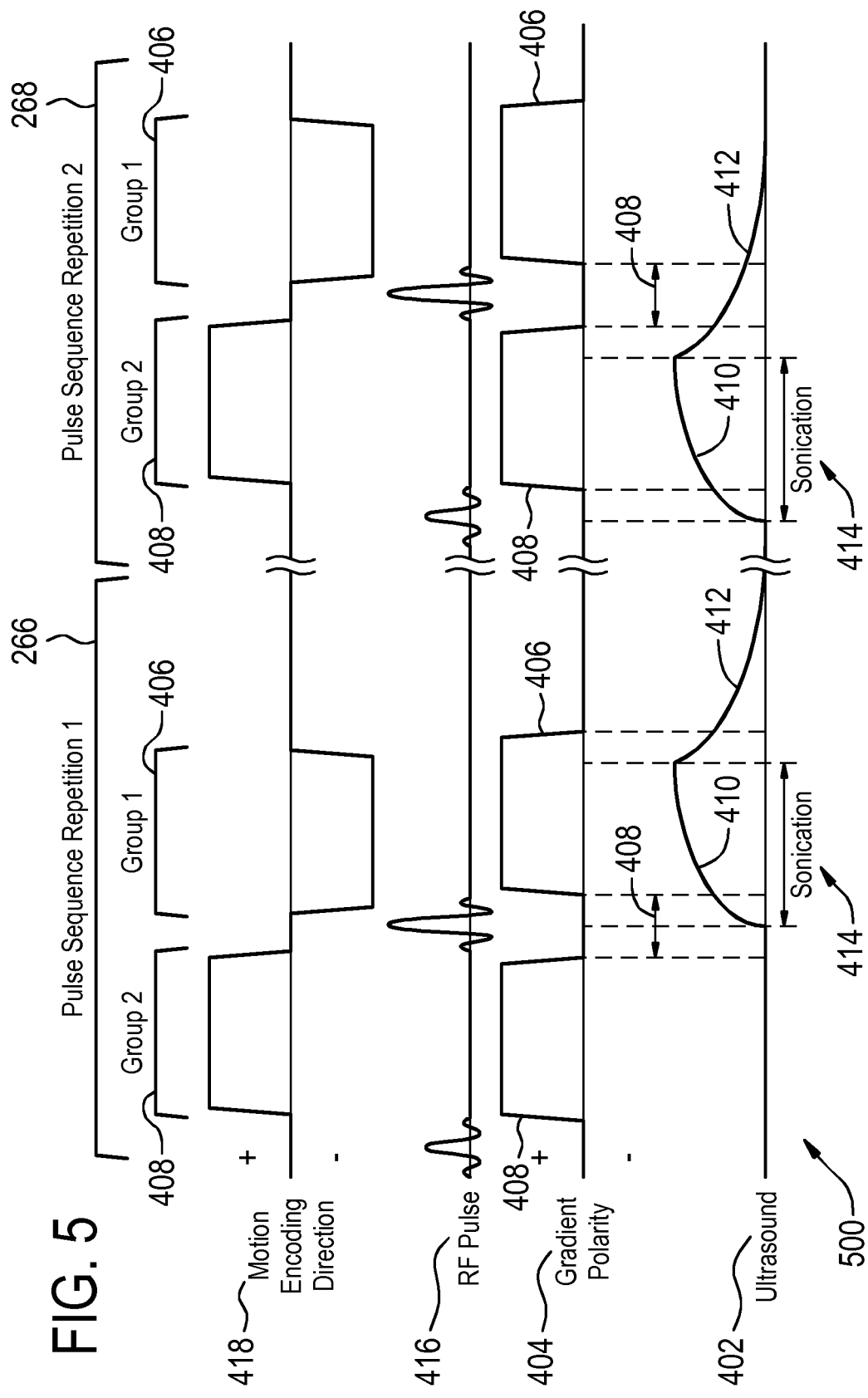
FIG. 5 shows a further example of a timing diagram that illustrates a spin echo magnetic resonance ARFI sequence.

FIG. 5 shows a further example of a timing diagram. In this example the timing diagram illustrates how to do a spin echo magnetic resonance ARFI sequence. In this example there is a static unipolar gradient but the ultrasound trigger is moved as was shown in FIG. 4. In this example the gradient polarity is always the same, however the motion encoding direction flips as it does with the timing diagram shown in FIG. 4.

Figure 6:
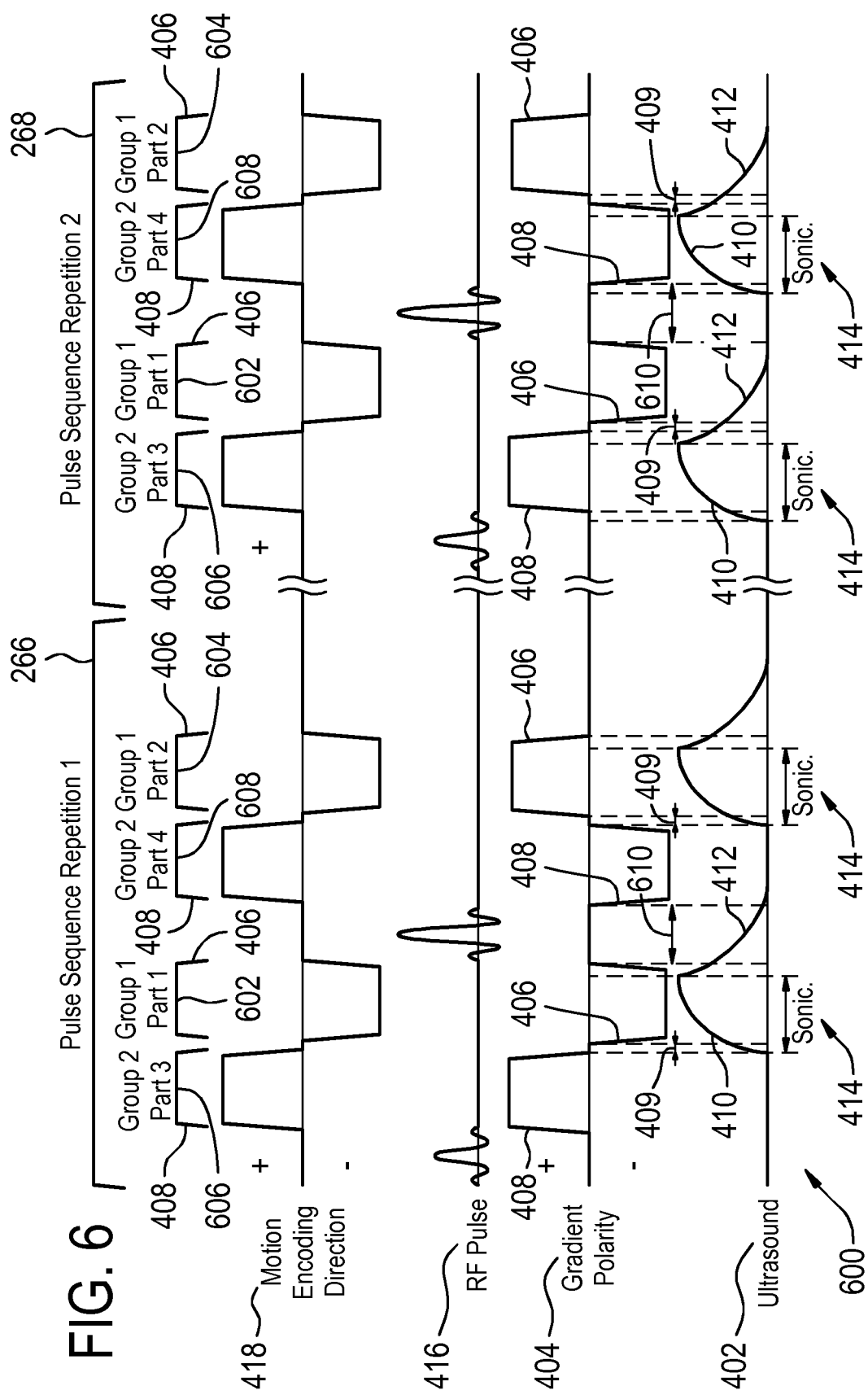
FIG. 6 shows a further example of a timing diagram which illustrates a spin echo magnetic ARFI sequence with static bipolar gradients.

FIG. 6 shows a further example of a timing diagram 600 which illustrates a spin echo magnetic ARFI sequence with static bipolar gradients. In this example this group of gradients 406 is further divided into a first part 602 and a second part 604. The second group of gradients 408 is divided into a third part 606 and a fourth part 608. As such the sonication in each pulse sequence repetition is performed twice. There is still a predetermined pause 409 between the first group 406 and the second group 408 but there is also additionally a predetermined pause 610 between the first part 602 and the fourth part 608.

In FIGS. 4, 5, and 6 only motion encoding gradients are represented, other gradients related to spatial encoding of MR images are not illustrated.

To improve High Intensity Focused Ultrasound (HIFU) treatments, MR-Acoustic Radiation Force Imaging (MR-ARFI) provides precise detection of the focal point and correction of tissue induced aberrations. MR-ARFI is based on synchronization of ultrasound pulses with MR motion encoding gradients to create a phase signal change. To isolate the phase signal change induced by ultrasound pulses negative and positive phase changes are acquired by switching the polarity of the gradients every dynamic. The alternative solution proposed to improve MR-ARFI quality, consists to change the trigger delay of ultrasound pulses at each dynamic. At each dynamics, as e.g. represented by the first and second groups of motion encoding gradients, the sonication is applied at a different trigger delay. The sonications are e.g. applied in the form of ultrasould pulses and in respective dynamics, the timing of the ultrasould pulse relative to the motion encoding gradient in its dynamic is different. The timing of the ultrasound pulse with the first motion encoding gradient is different from the timing of the ultrasound pulse with the second motion encoding gradient. In this way, in different dynamics, the ultrsound pulses coincide with gradient lobes each of different polarities of the equal polarity motion encoding gradient pulses.

The use of MR guided High Intensity Focused Ultrasound (MR-HIFU) is routinely used for several clinical applications. However those treatments are significantly affected by tissue heterogeneity defocusing the beam and shifting the location of the heating. MR Acoustic Radiation Force Imaging (MR-ARFI) allows quantification of micrometric displacement induced by ultrasound pulses which are proportional to the local acoustic intensity. The knowledge of the acoustic intensity distribution allows to measure aberration induced by tissue heterogeneities and thus to optimize heating efficiency in target location.

MR-ARFI relies on the quantification of tissue displacement induced by ultrasound pulses synchronized with MR motion encoding gradients. The phase shift $\varphi$ measured by MR-ARFI can be processed from the integration of the gradient amplitude $G_{(t)}$ multiply by the displacement $x(t)$:

$$\varphi = \int G_{(t)} x_{(t)} dt$$

The knowledge of the applied gradient amplitudes over time and the measured local phase variation allows processing of the average displacement distribution during the applied motion encoding gradients. However phase change measured can be also induced by artefacts generated by motion encoding gradients as well as the temperature variations induced by ultrasound pulses. For a gradient echo sequence, the polarity of the motion encoding gradients are systematically inverted every dynamics to induce opposite phase change $\varphi^+$ and $\varphi^-$ between even and odd dynamics. The ultrasound pulse can optionally start slightly before the motion encoding gradient to increase the average displacement measured. For the same reason a temporal delay can be also inserted between the positive and negative gradients of each dynamic.

To suppress spatial phase variation due to B0 magnetic field inhomogeneity and drift, the displacement maps are obtained from the phase difference of two successive dynamics $(\varphi^+ - \varphi^-)/2$. In addition thermal maps can be simultaneously processed from the average of two successive dynamics $(\varphi^+ + \varphi^-)/2$ as described references. The same technic of switching gradients polarity between even and odd dynamics is also used with spin echo sequence including either unipolar gradients or bipolar gradients.

The switching of motion encoding gradients polarity every dynamics is a source multiples images artefacts such as eddy current and rupture of MR image steady state. Since those artefacts change every dynamics, they can be miss-interpreted as a tissue displacement. Artefacts induced by switching motion encoding gradients are usually suppressed by subtraction of the apparent displacement measured prior to application of ultrasound pulses. First dynamics are used to create this reference displacement map based on $(\varphi 0+ - \varphi 0-)/2$. This reference technic introduces additional noise on the measured displacement maps (up to 40% SNR loss) and makes displacement mapping very sensitive to bulk motion of the patient in which case the reference displacement map is not aligned with the latest displacement maps.

The switching of motion encoding gradients polarity doesn't affect only the phase images but also the magnitude images. This magnitude image typically used for anatomical registration purpose is thus contaminated with unwanted contrasts changing every dynamics. Temporal averaging can be used to remove a minor part of this artefact on anatomical background images, but in this case the monitoring of patient motion is significantly delayed and blurred.

Instead of switching the polarity of the motion encoding gradient every dynamics, the proposed method consists to change the trigger delay of the ultrasound pulse every dynamics. MR-ARFI sequences (gradient echo or spin echo) are systematically composed of two symmetric series of positive and negative motion encoding gradients (repetition of unipolar or bipolar gradients). While one series of gradients is synchronized with ultrasound pulses to induce a phase change measuring the displacement, the other series of gradient is used to rewind the previous series of gradients to insure a null momentum. Maintain a null momentum of motion encoding gradient is essential to avoid unwanted shifting of the complete image in k space.

It is proposed to maintain MR image steady by using systematically the same motion encoding gradients for all dynamics. In this case the trigger delay can be set differently for even and odd dynamics in order to apply the ultrasound pulses during positive or negative parts of the motion encoding gradients for even and odd dynamics respectively. This method also provides quantification of opposite phase changes $\varphi^+$ and $\varphi^-$ between even and odd dynamics allowing simultaneous quantification of temperature and displacement without having artefacts related to alternated motion encoding gradients.

To illustrate this method, the FIG. 4 presents an example of ultrasound pulses aligned with the positive second gradient for even dynamics and the negative first gradient for odd dynamic, while maintaining the same motion encoding gradients for all dynamics.

This method offers the main advantage to keep a steady state in MR image encoding but as a drawback when the sonication pulse is applied during the first motion encoding gradient, some displacement remains during the second motion encoding gradient.

To show the importance of steady state on MR image, sequences described with alternated gradients and FIG. 4 (with static gradients) were acquired without applying any ultrasound pulses. The gradient duration was set to 4 ms with strength of 30.2 mT/s, ramp up of 0.155 ms and duration between both gradients of 2 ms. As comparative purpose, data were also acquired without any ARFI motion encoding gradients. The other acquisition parameters correspond to a standard thermal map sequence with an echo time of 20 ms.

As used herein a static gradient refers to the use of the same pulse sequence for both dynamics. In this case the pulse sequences are the same but the ultrasound is varied. When alternated or alternating gradients is referred to this refers to the state of the art where the ultrasound pulses in each dynamic remains the same but the gradients are flipped in the pulse sequence for controlling the magnetic resonance imaging system.

Figure 7:
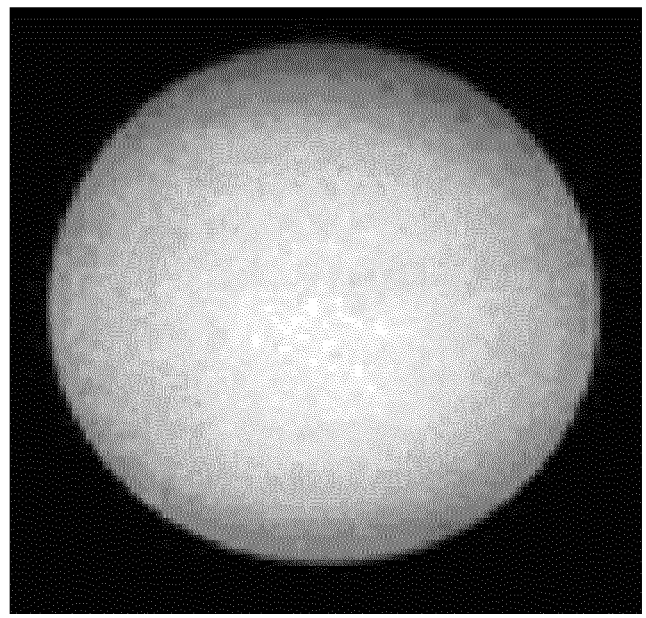
FIG. 7 shows a magnetic resonance magnitude image that was acquired when no ARFI gradients were used.

FIG. 7 shows a magnetic resonance magnitude image that was acquired when no ARFI gradients were used.

Figure 8:
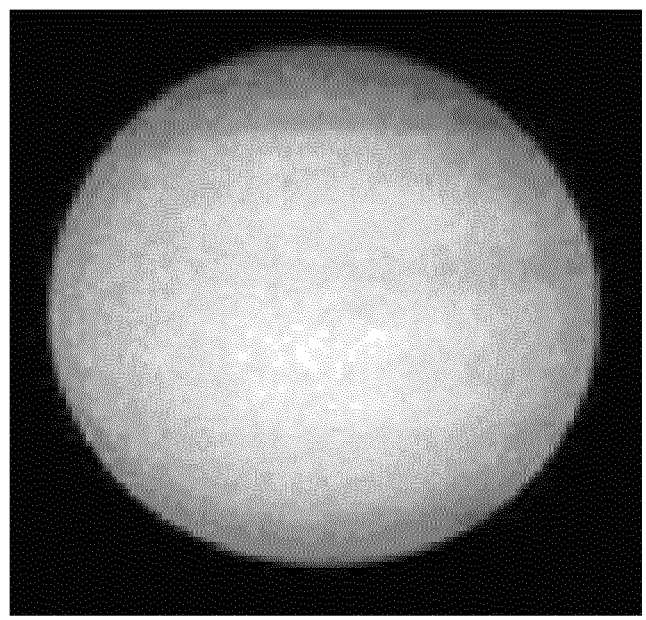
FIG. 8 shows a magnetic resonance image that was acquired with the static ARFI gradients.

FIG. 8 shows a magnetic resonance image that was acquired with the static ARFI gradients as is described herein.

Figure 9:
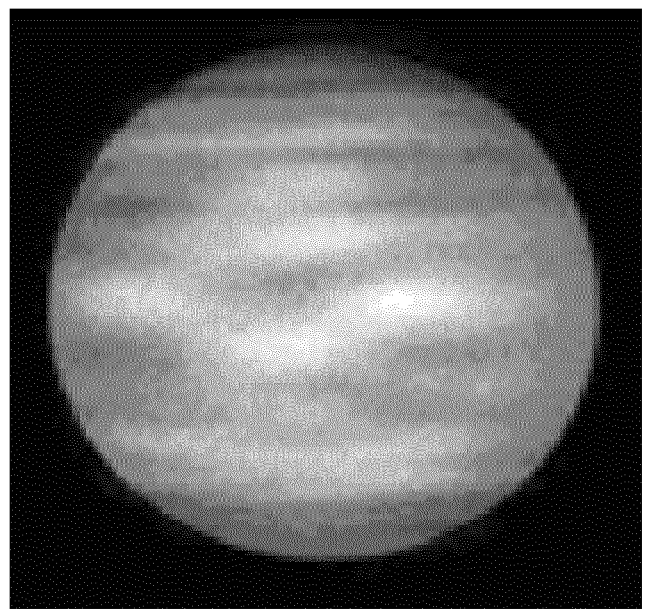
FIG. 9 shows a magnetic resonance image that was acquired when using the ARFI gradients where the gradients themselves are switching within the pulse sequence.

FIG. 9 shows the state of the art magnetic resonance image that was acquired when using the state of the art ARFI gradients where the gradients themselves are switching within the pulse sequence. It can be seen by comparing FIGS. 8 and 9 that there are many more artifacts within the image. This shows that it is beneficial to use the same pulse sequence commands but to vary the timing of the ultrasound instead.

The FIGS. 7, 8 and 9 show magnitude images acquired using a quality assistance phantom. Without any MR-ARFI gradients the magnitude signal inside this cylindrical phantom is rather homogenous (FIG. 7). However the use of alternating ARFI gradients drastically impact on this signal homogeneity (FIG. 9). The use of static ARFI gradients resolves most of the image deformation induced by the alternating ARFI gradients (FIG. 8).

Figure 10:
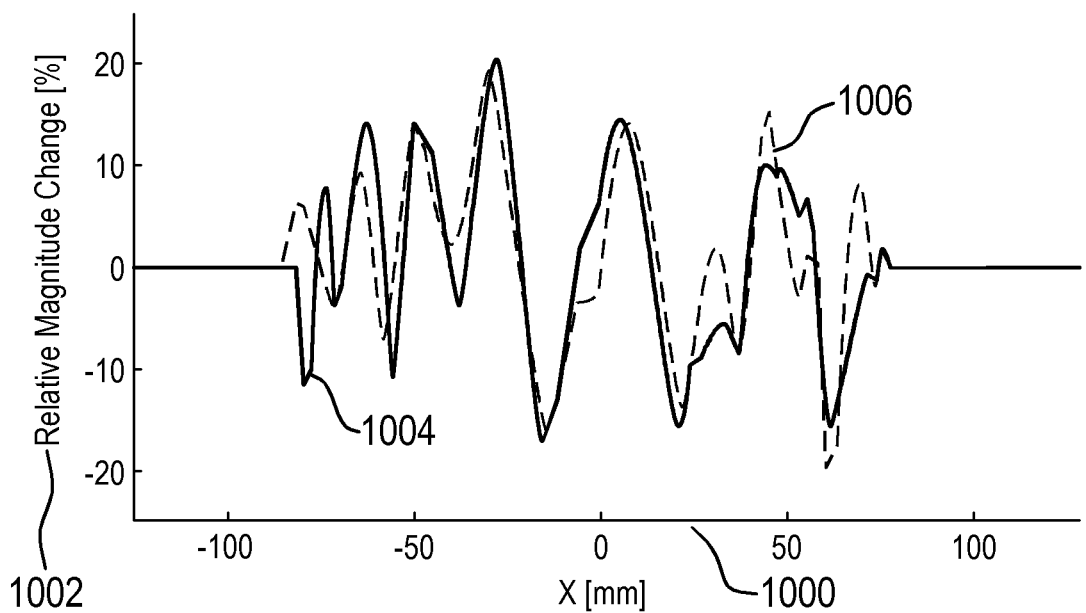
FIG. 10 shows the magnitude difference between the odd and even dynamics for FIG. 9 in the slice direction.
Figure 11:
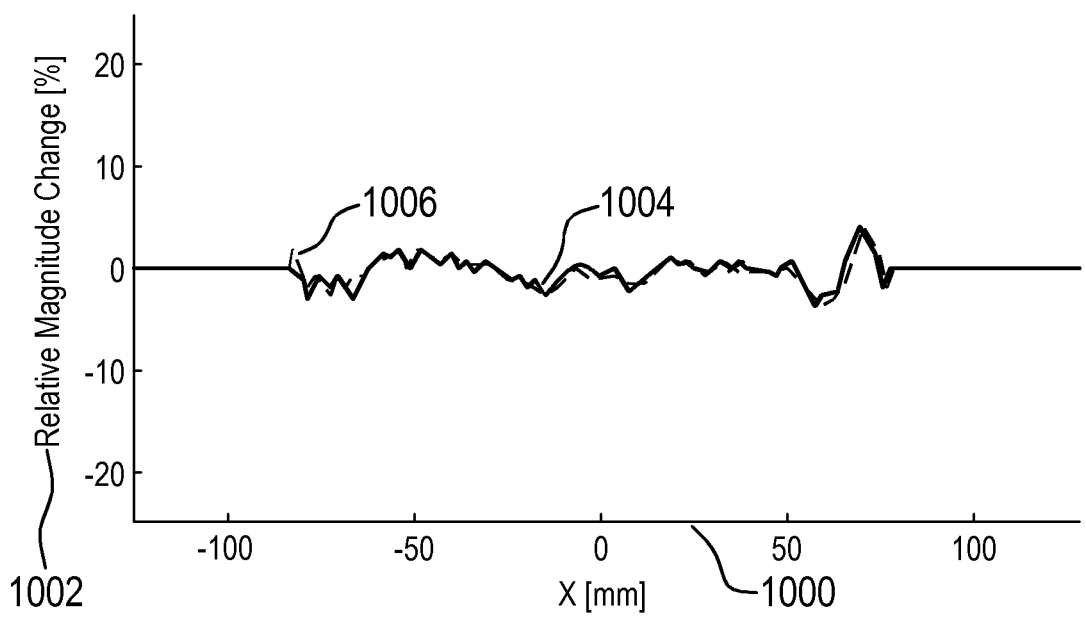
FIG. 11 shows the magnitude difference between the odd and even dynamics for FIG. 8 in the slice direction.
Figure 12:
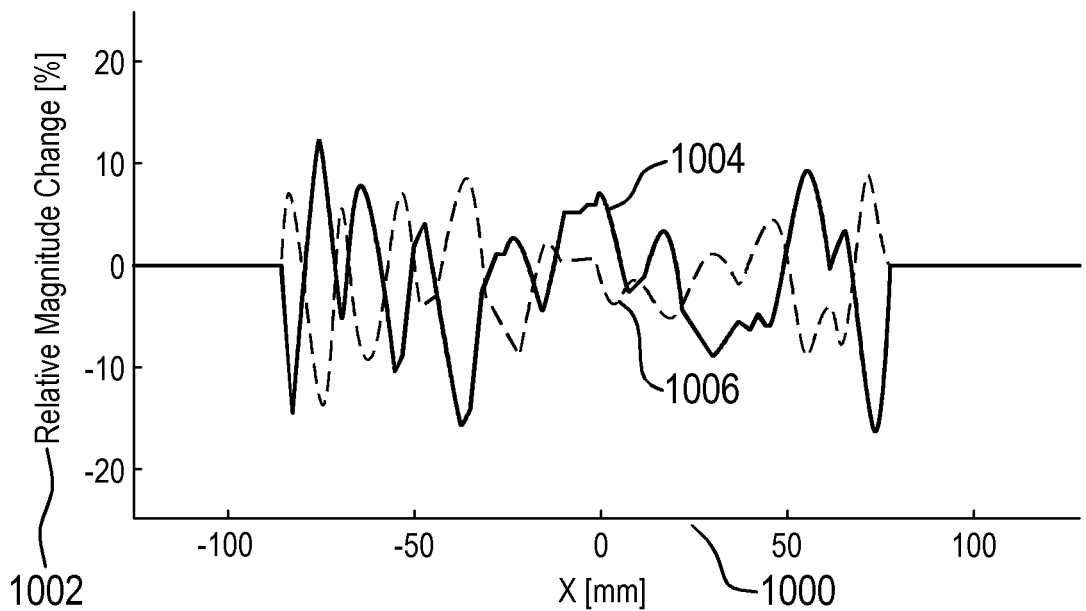
FIG. 12 shows the magnitude difference between the odd and even dynamics for FIG. 9 in the phase direction.
Figure 13:
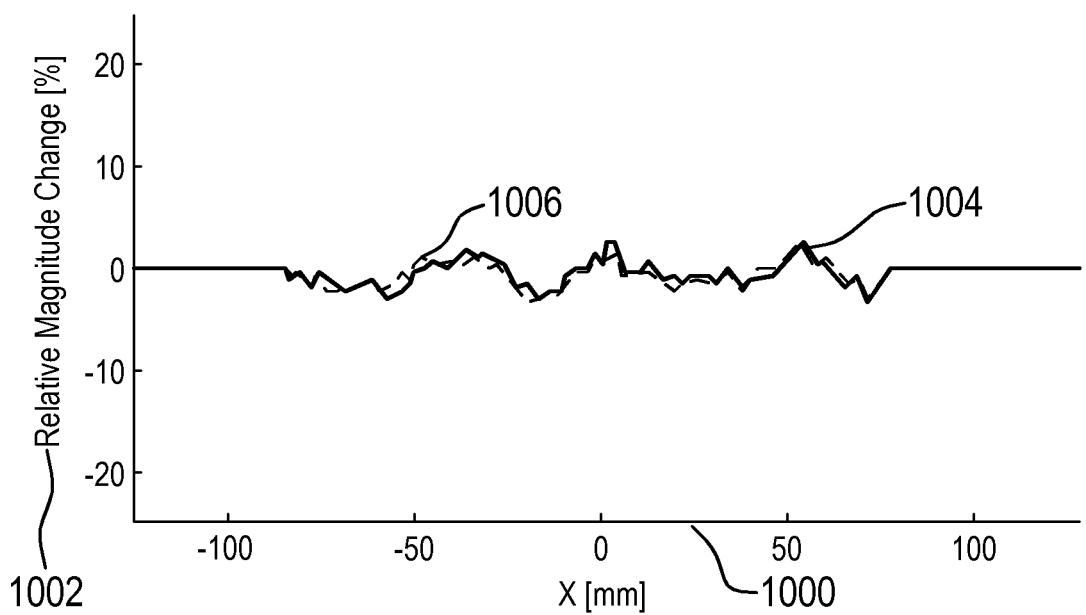
FIG. 13 shows the magnitude difference between the odd and even dynamics for FIG. 8 in the phase direction.
Figure 14:
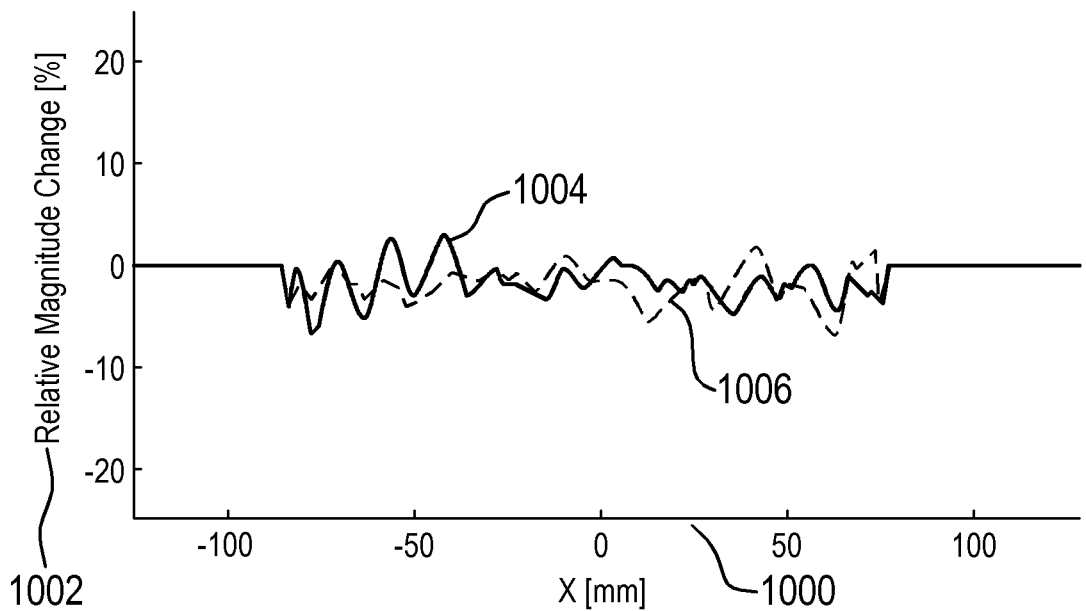
FIG. 14 shows the magnitude difference between the odd and even dynamics for FIG. 9 in the frequency direction.
Figure 15:
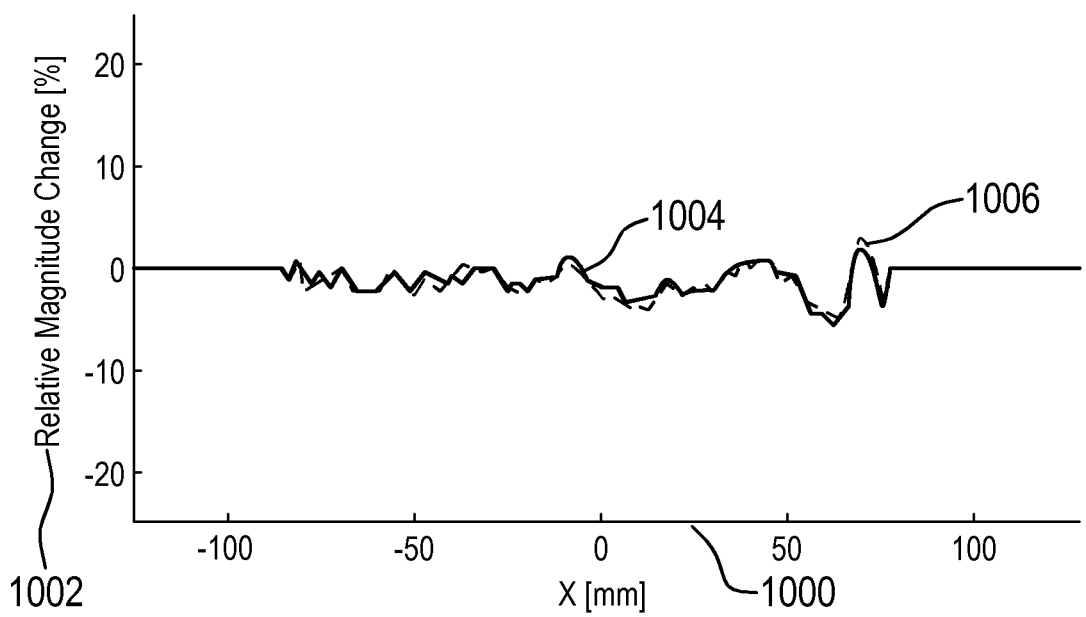
FIG. 15 shows the magnitude difference between the odd and even dynamics for FIG. 8 in the frequency direction.

FIGS. 10-15 show the magnitude difference with and without the ARFI gradients using alternate or static gradients for images 9 and 8. FIGS. 10, 12 and 14 correspond to FIG. 9. FIGS. 11, 13 and 15 correspond to FIG. 8. FIGS. 10, 12 and 14 are for the so called alternated gradients where within the pulse sequence the gradient is switched between the first dynamic 1004 and the second dynamic 1006. In FIGS. 11, 13 and 15 the gradients are not changed at all but the location of the sonication is changed instead. On each of the Figs. the data for a first dynamic 1004 and a second dynamic 1006 are labeled. The x-axis is the position 1000. The y-axis is the relative magnitude change 1002. FIGS. 10 and 11 show the case with motion encoding gradients aligned along the slice encoding direction. FIGS. 12 and 13 show the case with motion encoding gradients aligned along the phase encoding direction. FIGS. 14 and 15 show the case with motion encoding gradients aligned along the frequency encoding direction. From these Figs. it can be seen that the use of the so called static gradients results in fewer artifacts in the image.

FIGS. 10 to 15 provides a more detailed evaluation of the artefact induced by the alternating ARFI gradients on magnitude distribution along the phase image encoding direction which corresponds to the vertical axis of FIGS. 7, 8, and 9. For this analysis 50 dynamics were acquired using either alternating or static ARFI gradients and using motion encoding gradients aligned with either the slice, phase or frequency image encoding direction. The even and odd slices were averaged separately over 25 dynamics each to remove most of the white measurement noise. This spatial intensity profile of the magnitude was normalized relatively to the magnitude signal acquired without ARFI gradients. As consequence almost only the signal intensity change induced by the use of ARFI gradients is represented. The FIGS. 10 to 15 indicates that the intensity changes produces by the alternating ARFI gradients can reach up to 20% when the motion encoding gradient is aligned with slice and phase image encoding directions, but it remains much lower with static gradients. The magnitude signal is very different between even and odd dynamics while using alternating ARFI gradients (almost opposite spatial variations for frequency and phase image encoding directions). As expected static ARFI gradients don't indicates any significant difference of signal between even and odd dynamics since they are both acquired the same way.

Figure 16:
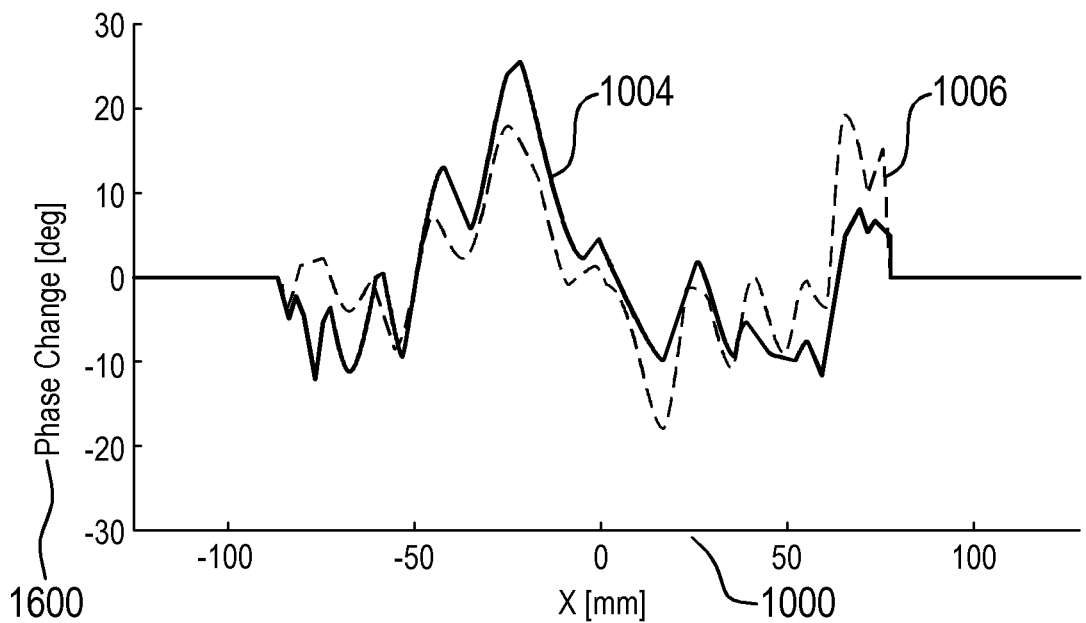
FIG. 16 shows the phase difference difference between the odd and even dynamics for FIG. 9 in the slice direction.
Figure 17:
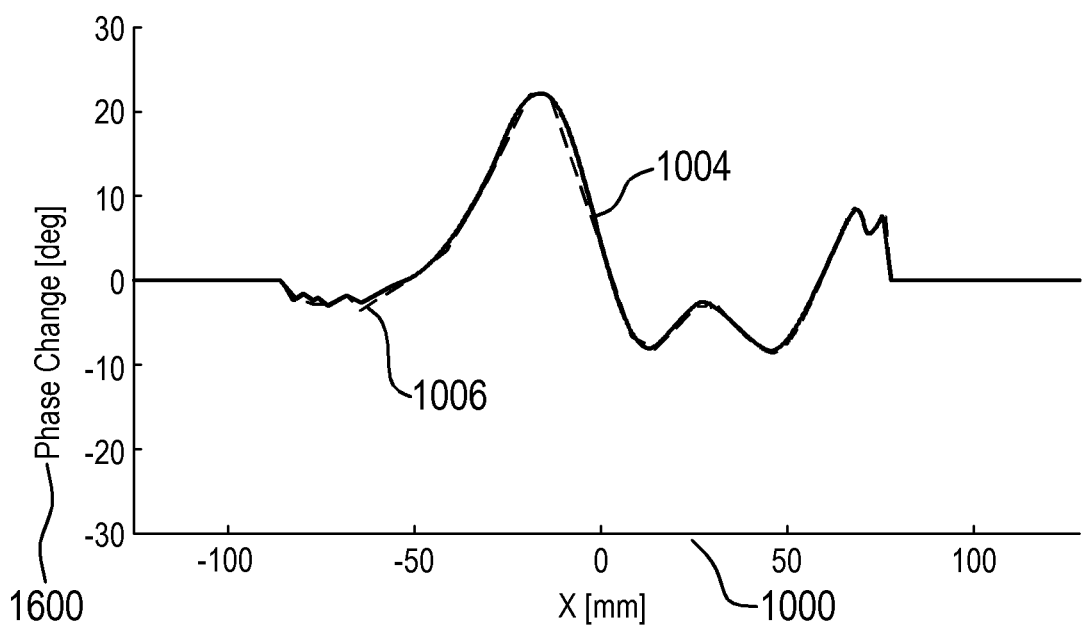
FIG. 17 shows the phase difference between the odd and even dynamics for FIG. 8 in the slice direction.
Figure 18:
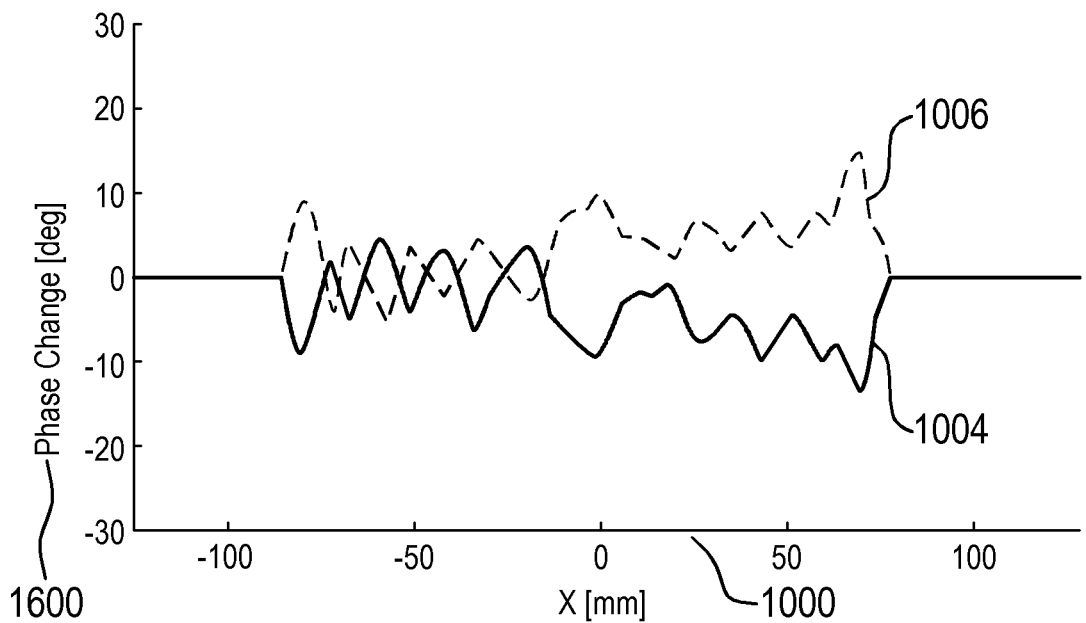
FIG. 18 shows the phase difference between the odd and even dynamics for FIG. 9 in the phase direction.
Figure 19:
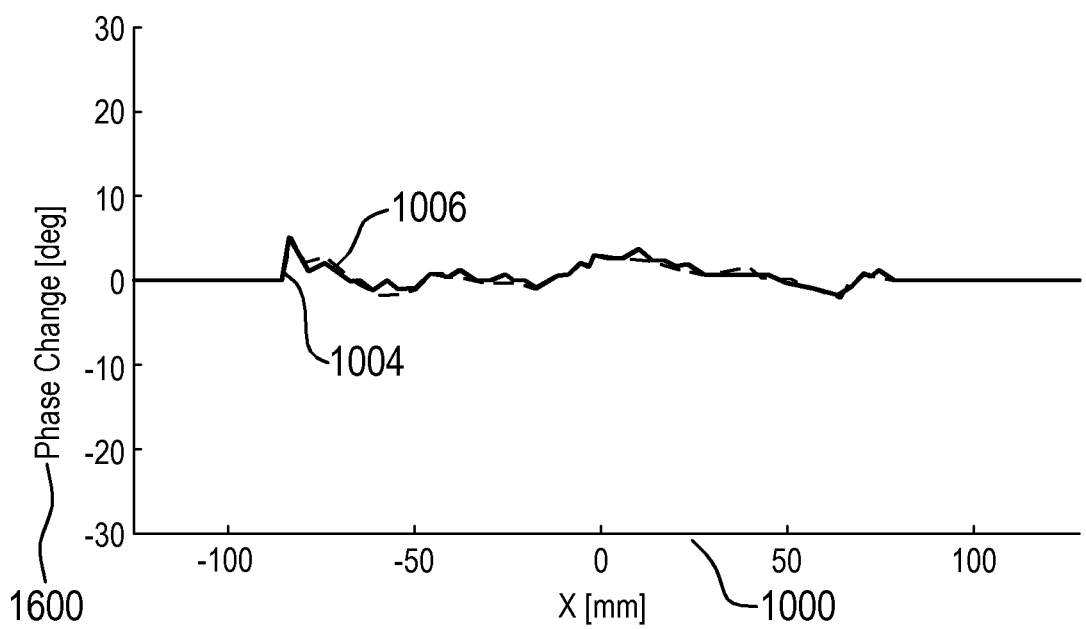
FIG. 19 shows the phase difference between the odd and even dynamics for FIG. 8 in the phase direction.
Figure 20:
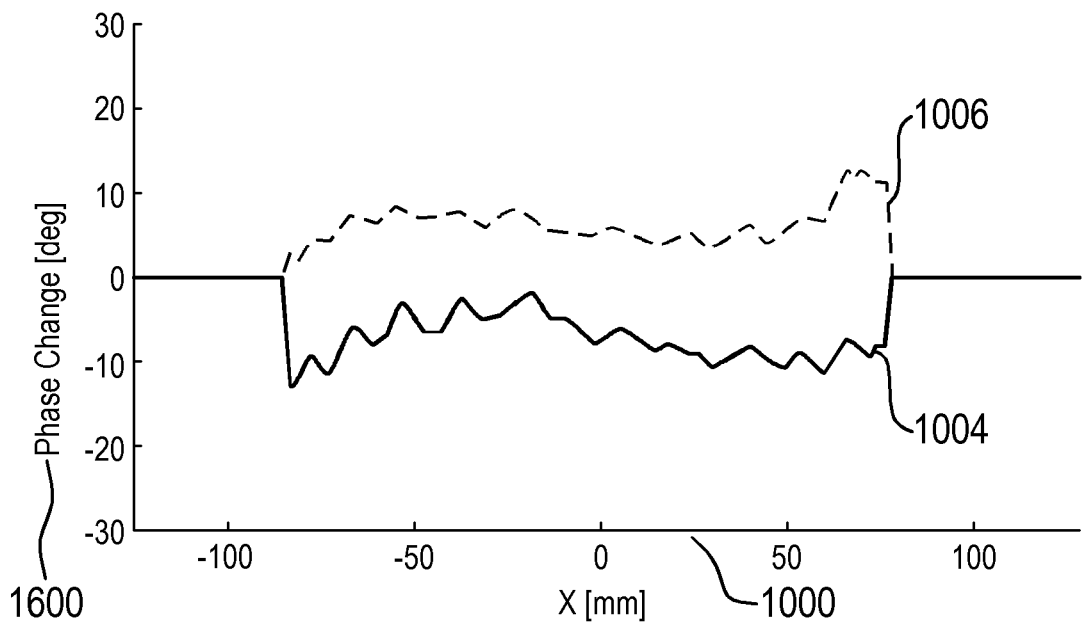
FIG. 20 shows the phase difference between the odd and even dynamics for FIG. 9 in the frequency direction.
Figure 21:
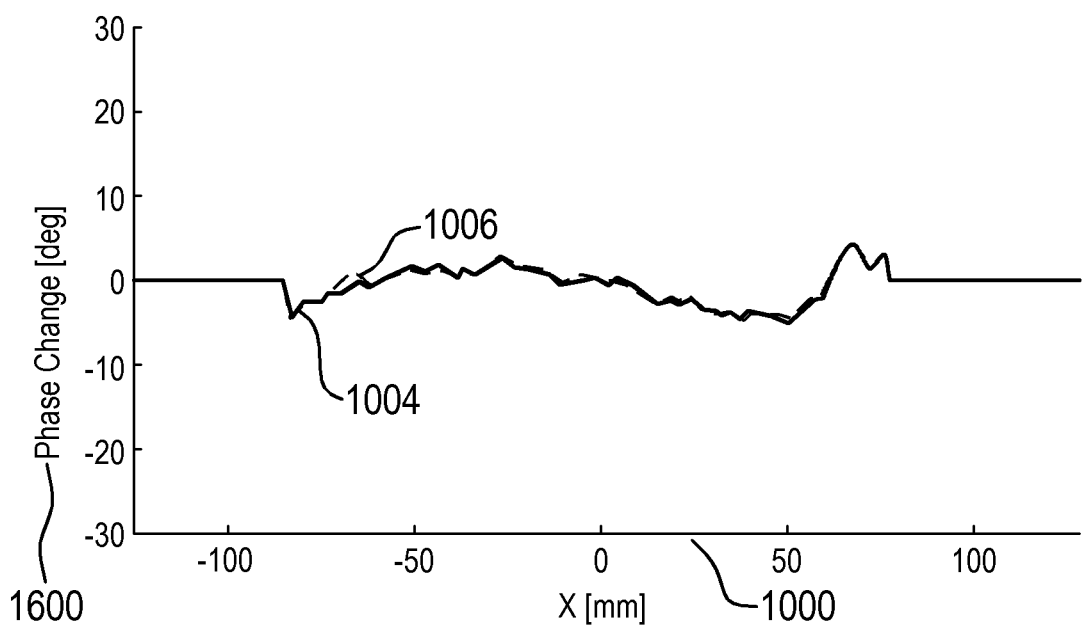
FIG. 21 shows the phase difference between the odd and even dynamics for FIG. 8 in the frequency direction.

FIGS. 16 to 21 are similar to FIGS. 10-15 except in FIGS. 16-21 the phase differences between image 8 and 9 are compared. FIGS. 17, 19 and 21 correspond to FIG. 8 and FIGS. 16, 18 and 20 correspond to FIG. 9. In FIGS. 17, 19 and 21 the phase change for the so called static gradients is displayed and in FIGS. 16, 18 and 20 the phase change for the alternating gradients is shown. In each Fig. there is the x-position 1000 and the phase change in degrees 1600. A first dynamic 1004 and a second dynamic 1006 is shown in each plot. FIG. 16 shows the change relative to slice direction for the alternating gradients. FIG. 17 shows the case of motion encoding gradients aligned along the slice direction for the static gradients. FIG. 18 shows the case of motion encoding gradients aligned along the phase direction for the alternating gradients. FIG. 19 shows the case of motion encoding gradients aligned along the phase direction for the static gradients. FIG. 20 shows the case of motion encoding gradients aligned along the frequency direction for the alternating gradients and FIG. 21 shows the case of motion encoding gradients aligned along the frequency direction for the static gradients.

Similar comparison for phase image is presented in FIGS. 16 to 21 in which the average phase image for even and odd dynamics are subtracted to the reference average phase acquired without ARFI gradients. Due to the B0 drift and different shimming occurring between each acquisition, an additional polynomial function has been fitted and subtracted to each phase image averaged over all dynamics. Similarly to the observation done for the magnitude image, the alternating ARFI gradients induce a strong change of the phase distribution. This phase variation is significantly different for even and odd dynamics.

Figure 22:
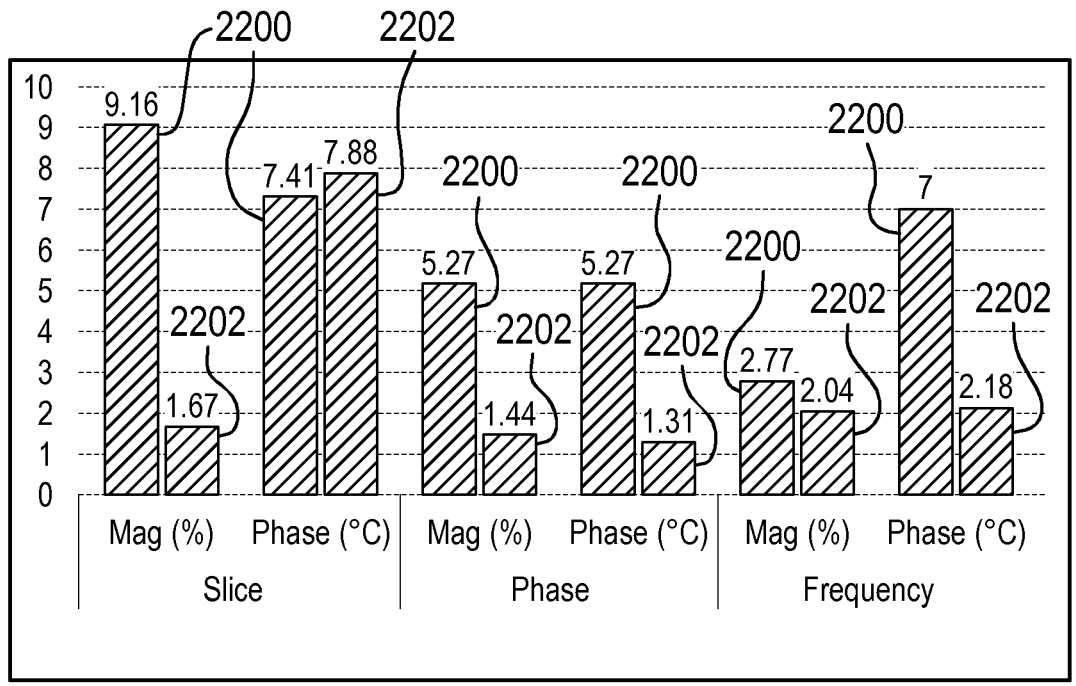
FIG. 22 shows the standard deviation of the difference between images with and without ARFI using alternating and static ARFI gradients.

FIG. 22 shows the standard deviation of the difference between images with and without ARFI using alternating 2200 and static 2202 ARFI gradients.

For a more quantitative estimation of the amplitude of the artefact induced by ARFI gradients, FIG. 22 indicates the standard deviation of the normalized magnitude and phase change for images acquired with alternating or static ARFI gradients with motion encoding gradients along each direction. With static gradient the artefact on magnitude image is reduced by a factor 4.24±1.15 and on the phase image by a factor 1.99±1.46.

Figure 23:
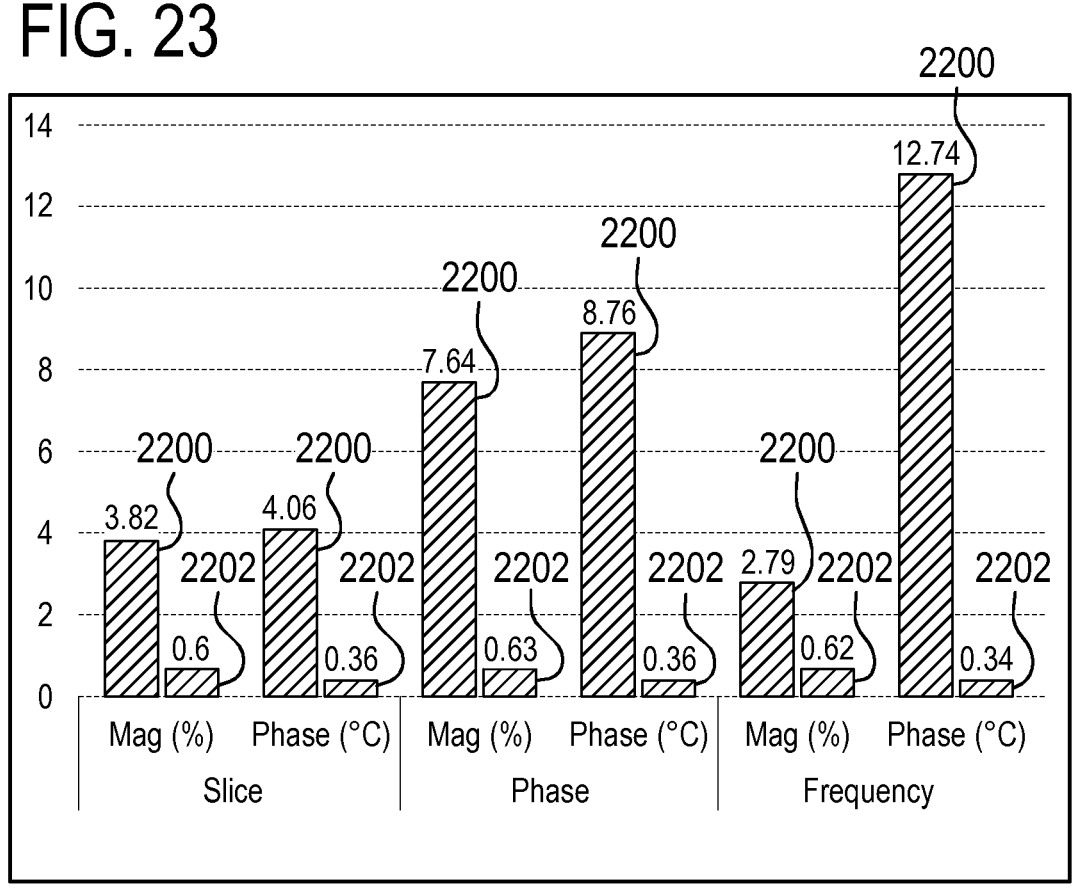
FIG. 23 shows the average difference between even and odd dynamics using alternating or static gradients.

FIG. 23 shows the average difference between even and odd dynamics using alternating 2200 or static 2202 gradients.

The average of the absolute difference between even and odd dynamics is presented FIG. 23. The use of static ARFI gradient reduces the change between even and odd dynamics on magnitude image is reduced by a factor 7.66±3.98 and on the phase image by a factor 24.36±13.1. In fact this result mainly depends on experimental setting such as the number of dynamic used because it is not expected to observe any difference other than white noise between two successive dynamics with static ARFI gradients.

The use of static gradients removes most the artefacts observed on magnitude and phase image observed with alternating gradients. In addition the static gradients ensure a perfect match of the background magnitude and phase image between even and odd dynamics. This image stability facilitates processing ARFI images and improves the robustness and accuracy of displacement mapping because no reference displacement map is necessary. The use of reference maps limits a lot clinical applications, for example this is the reason why the well-established PRF thermal mapping method is still not working for abdominal organs and researchers are still searching for alternative solutions.

Figure 24:
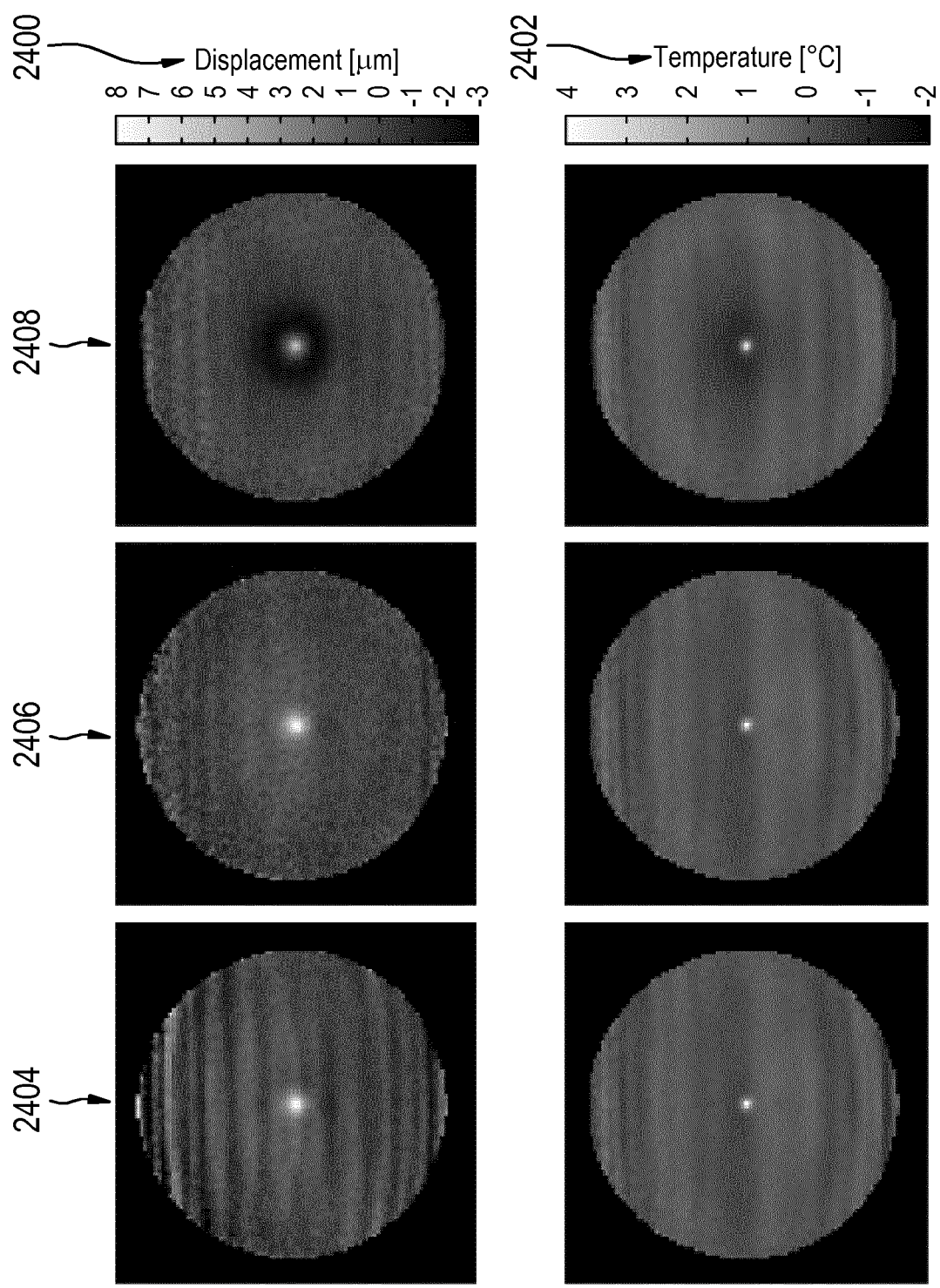
FIG. 24 shows plots of displacement maps and temperature maps.

FIG. 24 shows plots of displacement maps 2400 and temperature maps 2402. The displacement maps 2400 are in one row and the temperature maps 2402 are in another row. The first column 2404 shows the displacement 2400 and 2402 temperature map for use of alternating gradients. The middle column labeled 2406 shows the displacement 2400 and temperature map 2402 when alternating gradients with reference displacement are used. The right hand column 2408 shows a displacement map 2400 and temperature map 2402 when static gradients are used. In all FIGS. 100 watts AC power were applied. It can be seen that in the far right column 2408 there are fewer artifacts. Not only does the use of the static gradients improve the quality of the displacement map but it also improves the quality of the temperature mapping.

FIG. 24 shows displacement maps and thermal maps with alternated gradients (left), alternated gradients with reference displacement (center) and static gradients (right) using 100 Wac.

FIG. 24 presents the resulting displacement maps and thermal maps in this phantom with 100 Wac ultrasound pulses of 4 ms using alternated gradients, alternated gradients with a reference displacements maps and static gradients. Thermal maps are similar for those three methods. However ripples artefacts are produced by the alternated gradients on displacement maps. Most of those ripples artefacts can be removed by the use of a reference displacement map but at the cost of 41% additional noise introduced by this reference (without mentioning the sensitivity to bulk motion not present in this phantom example). The static gradient provides a displacement maps with a better SNR but also with a lower amplitude and a negative displacement around the focal point. This difference is due to the fact that application of ultrasound pulse during the first gradients doesn't decay completely in 2 ms before the second gradients with opposite sign. Because the tissue displacement widens overtime, due to share wave effect, the displacement distribution subtracted during the second gradient is larger than the one produce during the first gradient.

Figure 25:
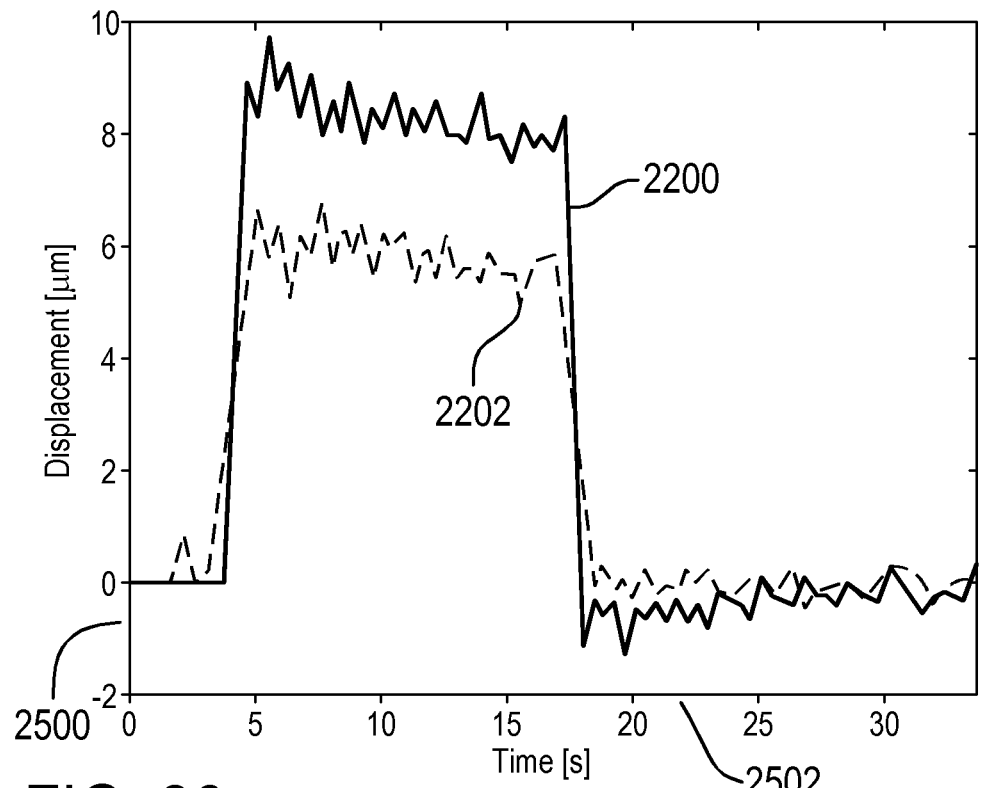
FIG. 25 shows the maximal displacement of a central target voxel as a function of time for both alternating gradients and static gradients.

FIG. 25 shows the maximal displacement 2500 as a function of time 2502. This is shown for the alternating gradients 2200 and the static gradients 2202.

Figure 26:
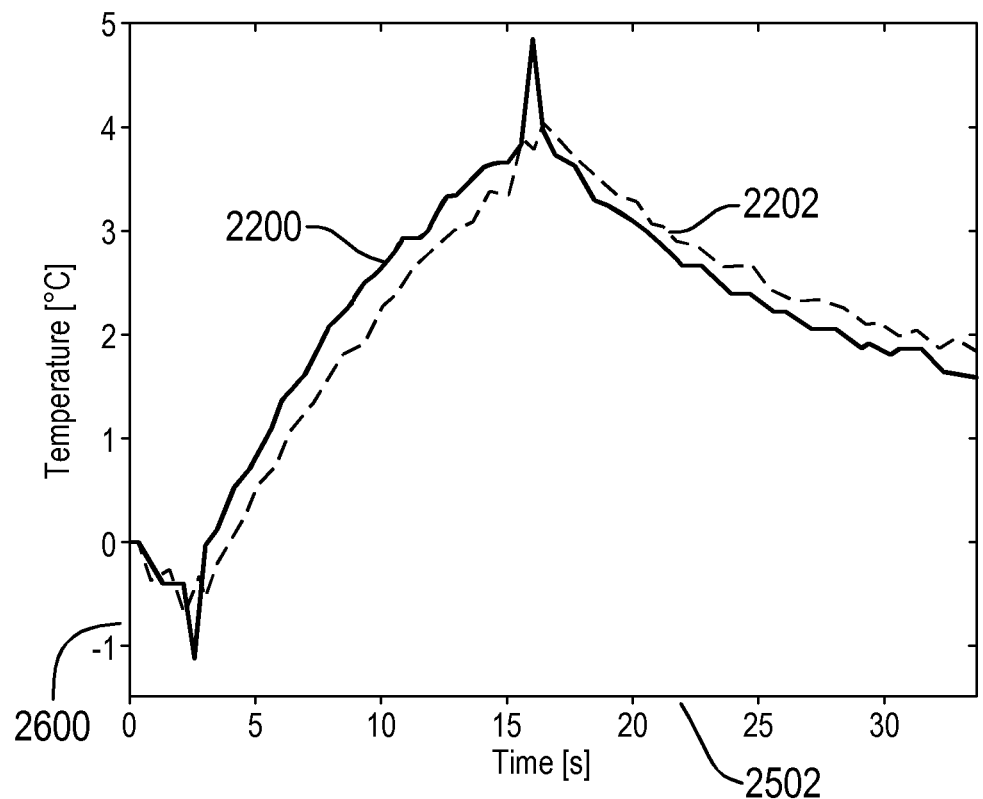
FIG. 26 shows the maximal temperature of a central target voxel as a function of time for both alternating gradients and static gradients.

FIG. 26 shows the maximum temperature 2600 as a function of time 2502. This is also shown for the alternating gradients 2200 and the static gradients 2202.

The FIG. 25 shows the temporal variation of the displacement and the temperature in the central target voxel. Both are similar except that the displacement and the temperature are under estimated with the use of static gradients partially due to the remaining of the displacement decay during the second gradients but also due to the ripple artefact at the location of the central voxel.

The amplitude of the temperature and displacement differences between static and alternated gradient can be quantified from the knowledge of the tissue displacement over time. The tissue displacement is described in the literature as an exponential rise and an exponential decay characterized by converging constant times $\tau_{rise}$=3.2 ms and $\tau_{decay}$=5.5 ms τrise for invivo muscle tissue. In the case of the sequence previously tested, it would result in a theoretical underestimation of the displacement by 20% and a temperature decay of 0.6° C. which is similar to values observed in FIGS. 25 and 26.

Once the tissue properties are known, the position of trigger delay can be fine-tuned to compensate for the thermal offset previously described.

The ultrasound pulse can be made to overlap by the same amount the first motion gradient encoding lobe for even dynamics than it overlaps the second motion encoding gradients on odd dynamics.

However to minimize the underestimation of the temperature and also the displacement (including negative displacements around the focal point) the most efficient method is simply to increase the duration between the first and second motion encoding gradients.

The usage of same motion encoding gradients for all dynamics, with a different ultrasound trigger delay for even and odd dynamics, can be also applied to spin echo sequence with unipolar gradients (FIG. 5) and bipolar gradients (FIG.

6). The use of spin echo unipolar motion encoding gradients provides the advantage of a long a duration between the first and second gradients due to the presence of an 180° RF pulse which avoids completely the underestimation of the displacement and the temperature with static ARFI gradients.

The use of this invention can be detected rapidly by looking at the homogeneity and stability of the magnitude of background images. Without this invention the background magnitude of MR-ARFI is contaminated with artefacts with a different pattern for even and odd dynamics flickering on every dynamics. The use of this invention can be also detected in a published article if it is described that no reference displacement map is used or if the SNR of the displacement measured is larger than the one expected for a known sequence. It is expected that this method will be systematically used for imaging of mobile organs without vital signal gating.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical apparatus
102 magnetic resonance imaging system
104 magnet
106 bore of magnet
108 imaging zone
110 magnetic field gradient coils
112 magnetic field gradient coils power supply
114 radio-frequency coil
116 transceiver
118 subject
120 subject support
122 high intensity focused ultrasound system
124 fluid filled chamber
126 ultrasound transducer
128 mechanism
130 mechanical actuator/power supply
132 path of ultrasound
134 ultrasound window
136 gel pad
138 sonication point or target zone
139 sonication region
140 beam axis
142 computer system
144 hardware interface
146 processor
148 user interface
150 computer storage
152 computer memory
260 pulse sequence commands
262 first sonication commands
264 second sonication commands
266 first magnetic resonance data
268 second magnetic resonance data
270 first motion encoded image
272 second motion encoded image
274 displacement map
276 temperature map
278 sonication pattern
280 control module
282 radiation force image reconstruction module
284 magnetic resonance thermometry reconstruction module
286 sonication pattern modification module
300 acquire first magnetic resonance data by controlling the magnetic resonance imaging system with the pulse sequence commands and by controlling the high intensity focused ultrasound system with the first sonication commands
302 acquire second magnetic resonance data by controlling the magnetic resonance imaging system with the pulse sequence commands and by controlling the high intensity focused ultrasound system with the second sonication commands
304 reconstruct a first motion encoded image from the first magnetic resonance data
306 reconstruct a second motion encoded image from the second magnetic resonance data
308 construct a displacement map from the difference of the first motion encoded image and the second motion encoded image
400 timing diagram
402 ultrasound
404 gradient polarity
406 first group
408 second group
409 predetermined delay
410 rise of sonication level
412 fall of sonication level
414 sonication period
416 radio frequency pulse
418 motion encoding direction
500 timing diagram
600 timing diagram
602 first part
604 second part
606 third part
608 fourth part
610 predetermined pause
1000 position
1002 relative magnitude change (percent change)
1004 first dynamic (odd dynamic)
1006 second dynamic (even dynamic)
1600 phase change (in degrees)
2200 alternating gradients
2202 static gradients
2400 displacement
2402 temperature
2404 alternated gradients
2406 alternated gradients with reference displacement
2408 static gradients 2500 displacement
2502 time
2600 temperature

The invention claimed is:

1. A medical apparatus, comprising:
a high intensity focused ultrasound system configured to sonicate a sonication region,
a magnetic resonance imaging system configured to acquire magnetic resonance data from an imaging zone, wherein the sonication region and the imaging zone at least partially overlap;
a processor configured to control the medical apparatus; and
a memory configured to store non-transitory machine executable instructions, wherein the memory further stores pulse sequence commands for controlling the magnetic resonance imaging system to acquire the magnetic resonance data according to an acoustic radiation force imaging protocol, wherein the memory further stores first sonication commands for controlling the high intensity focused ultrasound system to sonicate the sonication region according to the acoustic radiation force imaging protocol, wherein the memory further stores second sonication commands for controlling the high intensity focused ultrasound system to sonicate the sonication region according to the acoustic radiation force imaging protocol, wherein the pulse sequence commands specify the acquisition of the magnetic resonance data for first pulse sequence repetitions and second pulse sequence repetitions, wherein the pulse sequence commands specify for each of the first pulse sequence repetitions and the second pulse sequence repetitions a first group of motion encoding gradients and a second group of motion encoding gradients, wherein the first group of motion encoding gradients and the second group of motion encoding gradients are applied with the same polarity as each other, and wherein execution of the machine executable instructions causes the processor to:
acquire first magnetic resonance data by controlling the magnetic resonance imaging system with the pulse sequence commands and by controlling the high intensity focused ultrasound system with the first sonication commands, wherein the first sonication commands cause the high intensity focused ultrasound system to sonicate the sonication region during the first group of motion encoding gradients;
acquire second magnetic resonance data by controlling the magnetic resonance imaging system with the pulse sequence commands and by controlling the high intensity focused ultrasound system with the second sonication commands, wherein the second sonication commands cause the high intensity focused ultrasound system to sonicate the sonication region during the second group of motion encoding gradients,
apply first trigger delays to the first sonication commands within the first pulse sequence repetitions, and apply second trigger delays to the second sonication commands within the second pulse sequence repetitions, wherein the first trigger delays define a first timing of the first sonication commands within the first pulse repetitions, wherein the second trigger delays define a second timing of the second sonication commands within the second pulse repetitions, and wherein the first trigger delays are different than the second trigger delays;
reconstruct a first motion encoded image from the first magnetic resonance data;
reconstruct a second motion encoded image from the second magnetic resonance data; and
construct a displacement map from a difference between the first motion encoded image and the second motion encoded image.

2. The medical apparatus of claim 1, wherein the pulse sequence commands encode for displacement in a first direction during the first group of motion encoding gradients, wherein the pulse sequence commands encode for displacement in a second direction during the second group of motion encoding gradients, and wherein the first direction is opposite to the second direction.

3. The medical apparatus of claim 1, wherein the acoustic radiation force imaging protocol is a gradient echo acoustic radiation force imaging protocol.

4. The medical apparatus of claim 3, wherein execution of the non-transitory machine executable instructions further causes the processor to calculate a thermal map using the first magnetic resonance data and the second magnetic resonance data according to a proton resonance frequency shift method.

5. The medical apparatus of claim 1, wherein the acoustic radiation force imaging protocol is a spin echo acoustic radiation force imaging protocol.

6. The medical apparatus of claim 1,
wherein the pulse sequence commands specify that the first group of motion encoding gradients is divided into a first part and a second part,
wherein the pulse sequence commands specify that the second group of motion encoding gradients is divided into a third part and a fourth part,
wherein the pulse sequence commands specify that the first part and the second part have opposite polarities,
wherein the pulse sequence commands specify that the third part and the fourth part have opposite polarities, and
wherein the pulse sequence commands specify that the first part and the fourth part have identical polarities.

7. The medical apparatus of claim 6, wherein the pulse sequence commands specify a first predetermined pause of the motion encoding gradients between the first part and the third part, and wherein the pulse sequence commands specify a second predetermined pause of the motion encoding gradients between the second part and the fourth part.

8. The medical apparatus of claim 1, wherein the pulse sequence commands specify a predetermined delay of the motion encoding gradients between the first group of motion encoding gradients and the second group of motion encoding gradients.

9. The medical apparatus of claim 8, wherein the predetermined delay is any one of: between 1 ms and 20 ms, between 2 ms and 4 ms, between 3 ms and 5 ms, and between 4 ms and 6 ms.

10. The medical apparatus of claim 1, wherein execution of the machine executable instructions causes the processor to perform any one of:
acquire the first magnetic resonance data and the second magnetic resonance data sequentially, and
acquire the first magnetic resonance data and the second magnetic resonance data by interleaving acquisition of lines of k-space.

11. The medical apparatus of any one of claim 1, wherein execution of the non-transitory machine executable instructions further causes the processor to:
- receive a sonication pattern; and
- modify the sonication pattern using the displacement map.

12. A method of operating a medical apparatus, wherein the medical apparatus comprises a high intensity focused ultrasound system for sonicating a sonication region, wherein the medical apparatus further comprises a magnetic resonance imaging system for acquiring magnetic resonance data from an imaging zone, wherein the sonication region and the imaging zone at least partially overlap, wherein the method comprises:
- acquiring first magnetic resonance data by controlling the magnetic resonance imaging system with pulse sequence commands and by controlling the high intensity focused ultrasound system with first sonication commands, wherein the pulse sequence commands control the magnetic resonance imaging system to acquire the magnetic resonance data according to an acoustic radiation force imaging protocol, wherein the pulse sequence specifies the acquisition of the magnetic resonance data for first pulse sequence repetitions and second pulse sequence repetitions, wherein the pulse sequence commands specify for each of the first pulse sequence repetitions and the second pulse sequence repetitions a first group of motion encoding gradients and a second group of motion encoding gradients, wherein the first group of motion encoding gradientsand the second group of motion encoding gradients are applied with the same polarity as each other, and wherein the first sonication commands cause the high intensity focused ultrasound system to sonicate the sonication region during the first group of motion encoding gradients according to the acoustic radiation force imaging protocol;
- acquiring second magnetic resonance data by controlling the magnetic resonance imaging system with the pulse sequence commands and by controlling the high intensity focused ultrasound system with second sonication commands, wherein the second sonication commands cause the high intensity focused ultrasound system to sonicate the sonication region during the second group of motion encoding gradients according to the acoustic radiation force imaging protocol;
- applying first trigger delays to the first sonication commands within the first pulse sequence repetitions, and applying second trigger delays to the second sonication commands within the second pulse sequence repetitions, wherein the first trigger delays define a first timing of the first sonication commands within the first pulse repetitions, wherein the esecond trigger delays define a second timing of the second sonication commands within the second pulse reprtitions, and wherein the first trigger delays are different than the second trigger delays;
- reconstructing a first motion encoded image from the first magnetic resonance data;
- reconstructing a second motion encoded image from the second magnetic resonance data; and
- constructing a displacement map from a difference between the first motion encoded image and the second motion encoded image.

13. The method of claim 12, wherein the pulse sequence commands encode for displacement in a first direction during the first group of motion encoding gradients, wherein the pulse sequence commands encode for displacement in a second direction during the second group of motion encoding gradients, and wherein the first direction is opposite to the second direction.

14. The method of claim 13, further comprising calculating a thermal map using the first magnetic resonance data and the second magnetic resonance data according to a proton resonance frequency shift method.

15. The method of claim 12, wherein the acoustic radiation force imaging protocol is a gradient echo acoustic radiation force imaging protocol.

16. The method of claim 12, wherein the acoustic radiation force imaging protocol is a spin echo acoustic radiation force imaging protocol.

17. The method of claim 12,
- wherein the pulse sequence commands specify that the first group of motion encoding gradients is divided into a first part and a second part,
- wherein the pulse sequence commands specify that the second group of motion encoding gradients is divided into a third part and a fourth part,
- wherein the pulse sequence commands specify that the first part and the second part have opposite polarities,
- wherein the pulse sequence commands specify that the third part and the fourth part have opposite polarities, and
- wherein the pulse sequence commands specify that the first part and the fourth part have identical polarities.

18. The method of claim 17, wherein the pulse sequence commands specify a first predetermined pause of the motion encoding gradients between the first part and the third part, and wherein the pulse sequence commands specify a second predetermined pause of the motion encoding gradients between the second part and the fourth part.

19. The method of claim 12, wherein the pulse sequence commands specify a predetermined delay of the motion encoding gradients between the first group of motion encoding gradients and the second group of motion encoding gradients.

20. A non-transitory computer readable medium having stored thereon machine executable instructions for execution by a processor controlling a medical apparatus, wherein the medical apparatus comprises: a high intensity focused ultrasound system for sonicating a sonication region, wherein the medical apparatus further comprises a magnetic resonance imaging system for acquiring magnetic resonance data from an imaging zone, wherein the sonication region and the imaging zone at least partially overlap, and wherein execution of the machine executable instructions causes the processor to:
- acquire first magnetic resonance data by controlling the magnetic resonance imaging system with pulse sequence commands and by controlling the high intensity focused ultrasound system with first sonication commands, wherein the pulse sequence commands cause the magnetic resonance imaging system to acquire the first magnetic resonance data according to an acoustic radiation force imaging protocol, wherein the pulse sequence commands specify the acquisition of the magnetic resonance data for first and second pulse sequence repetitions, wherein the pulse sequence commands specify for each of the pulse sequence repetitions a first group of motion encoding gradients and a second group of motion encoding gradients, wherein the first group of motion encoding gradients and the second group of motion encoding gradients are applied with the same polarity as each other, and wherein the first sonication commands cause the high intensity focused ultrasound system to sonicate the sonication region during the first group of motion encoding gradients according to the acoustic radiation force imaging protocol;

acquire second magnetic resonance data by controlling the magnetic resonance imaging system with the pulse sequence commands and by controlling the high intensity focused ultrasound system with second sonication commands, wherein the second sonication commands cause the high intensity focused ultrasound system to sonicate the sonication region during the second group of motion encoding gradients according to the acoustic radiation force imaging protocol;

apply first trigger delays to the first sonication commands within the first pulse sequence repetitions, and apply second trigger delays to the second sonication commands within the second pulse sequence repetitions, wherein the first trigger delays define a first timing of the first sonication commands within the first pulse repetitions, wherein the second trigger delays define a second timing of the second sonication commands within the second pulse repetitions, and wherein the first trigger delays are different than the second trigger delays;

reconstruct a first motion encoded image from the first magnetic resonance data;

reconstruct a second motion encoded image from the second magnetic resonance data; and construct a displacement map from a difference between the first motion encoded image and the second motion encoded image.

* * * * *